United States Patent
Sakurai et al.

(10) Patent No.: US 10,011,623 B2
(45) Date of Patent: *Jul. 3, 2018

(54) ALKOXIDE COMPOUND, THIN FILM-FORMING STARTING MATERIAL, AND THIN FILM FORMATION METHOD

(71) Applicant: ADEKA CORPORATION, Tokyo (JP)

(72) Inventors: Atsushi Sakurai, Tokyo (JP); Masako Hatase, Tokyo (JP); Tomoharu Yoshino, Tokyo (JP); Masaki Enzu, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,755

(22) PCT Filed: Jul. 16, 2015

(86) PCT No.: PCT/JP2015/070385
§ 371 (c)(1),
(2) Date: Dec. 14, 2016

(87) PCT Pub. No.: WO2016/021385
PCT Pub. Date: Feb. 11, 2016

(65) Prior Publication Data
US 2017/0129912 A1    May 11, 2017

(30) Foreign Application Priority Data
Aug. 5, 2014    (JP) .................. 2014-159270

(51) Int. Cl.
C07F 15/06    (2006.01)
C07F 15/04    (2006.01)
(Continued)

(52) U.S. Cl.
CPC .......... *C07F 15/065* (2013.01); *C07C 251/08* (2013.01); *C07C 251/76* (2013.01);
(Continued)

(58) Field of Classification Search
None
See application file for complete search history.

(56) References Cited

U.S. PATENT DOCUMENTS 3,869,278 A    3/1975 Wilcox
3,941,777 A    3/1976 Madsen et al.
(Continued)

FOREIGN PATENT DOCUMENTS

DE    32 28 099    2/1984
GB    1027265    4/1966
(Continued)

OTHER PUBLICATIONS

Friestad J Org Chem 2004 69-3 p. 863-875 (Year: 2004).*
(Continued)

*Primary Examiner* — Joseph A Miller, Jr.
(74) *Attorney, Agent, or Firm* — Wenderoth, Lind & Ponack, L.L.P.

(57) ABSTRACT

The alkoxide compound of the present invention is characteristically represented by the following general formula (I):

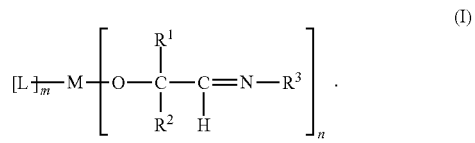

2 Claims, 5 Drawing Sheets

(51) Int. Cl.
　　　C07C 251/08　　(2006.01)
　　　C07F 7/08　　　(2006.01)
　　　C07C 251/76　　(2006.01)
　　　C07F 7/10　　　(2006.01)
　　　C23C 16/18　　 (2006.01)

(52) U.S. Cl.
　　　CPC ............. *C07F 7/0818* (2013.01); *C07F 7/10* (2013.01); *C07F 15/04* (2013.01); *C07F 15/045* (2013.01); *C07F 15/06* (2013.01); *C23C 16/18* (2013.01)

(56) References Cited

U.S. PATENT DOCUMENTS

| | | |
|---|---|---|
| 4,237,069 A | 12/1980 | Ulmer et al. |
| 4,310,634 A | 1/1982 | McEntire et al. |
| 4,952,479 A | 8/1990 | Aono et al. |
| 6,096,689 A | 8/2000 | Zagar et al. |
| 2008/0171890 A1 | 7/2008 | Kim et al. |
| 2014/0161977 A1 | 6/2014 | Winter et al. |
| 2014/0227444 A1 | 8/2014 | Winter et al. |
| 2015/0175642 A1 | 6/2015 | Sakurai et al. |

FOREIGN PATENT DOCUMENTS

| | | |
|---|---|---|
| GB | 1 537 828 | 1/1979 |
| JP | 49-55833 | 5/1974 |
| JP | 49-94618 | 9/1974 |
| JP | 51-119614 | 10/1976 |
| JP | 56-29559 | 3/1981 |
| JP | 58-65257 | 4/1983 |
| JP | 59-174834 | 10/1984 |
| JP | 11-508891 | 8/1999 |
| JP | 2006-328019 | 12/2006 |
| JP | 2008-537947 | 10/2008 |
| KR | 10-0675983 | 1/2007 |
| WO | 03/078581 | 9/2003 |
| WO | 2014/077089 | 5/2014 |

OTHER PUBLICATIONS

Makhviladze International Conference on Micro- and Nano-Electronics 2009, 75211A-1-A-12. (Year: 2009).*

Zandbergen-Tetrahedron V48 No. 19 p. 3977-3982 1992 (Year: 1992).*

International Search Report dated Oct. 13, 2015 in International (PCT) Application No. PCT/JP2015/070385.

Kalutarage et al., "Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films", Journal of the American Chemical Society, 135(34):12588-12591 (2013).

Nechaev et al., "Initiation of ethylene polymerization on organoelement cations $L_2MMe^+$ (M=Ge,Sn) with intramolecular coordination bonds: a theoretical study", Russian Chemical Bulletin, International Edition, 57(7):1364-1373 (2008).

Zandbergen et al., "A One-Pot Reduction-Transimination-Reduction Synthesis of N-substituted β-Ethanolamines from Cyanohydrins", Tetrahedron, 48(19):3977-3982 (1992).

Extended European Search Report dated Feb. 16, 2018 in European Application No. 15829762.2.

Gregory K. Friestad et al., "Diastereoselective Vinyl Addition to Chiral Hydrazones via Tandem Thiyl Radical Addition and Silicon-Tethered Cyclization", Organic Letters, 2000, vol. 2, No. 6, pp. 4237-4240.

Yoshikazu Makioka et al., "Lanthanoid Metal Promoted Reaction of Diaryl Ketones and Thioketones with Isocyanides", Chmiestry Letters, 1995, pp. 821-822.

Vanda Cerè et al., "Nucleophilic Addition of Organometallic Reagents to N,N-Dimethyl- and *SAMP*-Glyoxal-Monohydrazones", Tetrahedron, 1999, vol. 55, pp. 1087-1098.

Vanda Cerè et al., "Indium-Mediated Allylation of the N,N-Dimethyl Glyoxal Mono-Hydrazone: One-Pot Synthesis of Bis-Homoallyl, and of Homoallyl-Alkyl 1,2-Diols", Synlett, 1999, No. 10, pp. 1585-1587.

Takuya Itoh et al., "Stereo structure of Komodoquinone A, a Neuritogenic Anthracycline, from Marine *Streptomyces* sp. K53", Chem. Pharm. Bull., 2003, vol. 51, No. 12, pp. 1402-1404.

* cited by examiner

R1;wR2:0.0277;0.0636

R1;wR2:0.0277;0.0636

ALKOXIDE COMPOUND, THIN FILM-FORMING STARTING MATERIAL, AND THIN FILM FORMATION METHOD

TECHNICAL FIELD

The present invention relates to a novel alkoxide compound, a thin film-forming starting material containing this compound, a thin film formation method that uses this thin film-forming starting material, and a novel alcohol compound.

BACKGROUND ART

Thin film materials containing metal elements exhibit electrical characteristics, optical characteristics and the like, and are thus used in a variety of applications. For example, copper and copper-containing thin films exhibit the properties of a high electrical conductivity, a high resistance to electromigration, and a high melting point and as a result are used as LSI interconnect materials. In addition, nickel and nickel-containing thin films are used mainly, for example, for electronic component members, e.g., resistive films and barrier films, for recording media members, e.g., magnetic films, and for members for thin-film solar cells, e.g., electrodes. Moreover, cobalt and cobalt-containing thin films are used, for example, for electrode films, resistive films, adhesive films, magnetic tapes, and carbide tool members.

The methods for producing these thin films can be exemplified by sputtering methods, ion plating methods, MOD methods such as coating-pyrolysis methods and sol-gel methods, and chemical vapor deposition methods. However, chemical vapor deposition (also referred to hereafter simply as CVD), which includes atomic layer deposition (ALD), is the optimal production process because it has a number of advantages, e.g., it offers excellent composition controllability and an excellent step coverage capability, it supports mass production, and it enables hybrid integration.

A large number of diverse starting materials have been reported for the metal source used in chemical vapor deposition. For example, Patent Document 1 discloses a tertiary aminoalkoxide compound of nickel that can be used as a starting material for forming a nickel-containing thin film by metal-organic chemical vapor deposition (MOCVD). Also, Patent Document 2 discloses a tertiary aminoalkoxide compound of cobalt that can be used as a starting material for forming a cobalt-containing thin film by MOCVD. Further, Patent Document 3 discloses a tertiary aminoalkoxide compound of copper that can be used as a starting material for forming a copper-containing thin film by chemical vapor deposition. Non-Patent Document 1 discloses tertiary imidoalkoxide compounds of copper, nickel, cobalt, iron, manganese, and chromium.

PRIOR ART DOCUMENTS

Patent Documents

Patent Document 1: Japanese Patent Laid-Open No. 2008-537947

Patent Document 2: Korean Patent Registration No. 10-0675983

Patent Document 3: Japanese Patent Laid-Open No. 2006-328019

Non-Patent Documents

Non-Patent Document 1: J. Am. Chem. Soc., 2013, 135, 12588-12591

SUMMARY OF THE INVENTION

Problems to be Solved by the Invention

When a metal-containing thin film is formed on a substrate surface by vaporizing, for example, a chemical vapor deposition starting material, in order to minimize damage to the substrate by the heat applied during thin film formation and in order to minimize the energy required for thin film formation, a material is required that can form the thin film by undergoing thermal decomposition at low temperatures. The material is also required to not undergo autoignition from a safety standpoint and to have a low melting point based on transport considerations. In the particular case of formation of a metal thin film through the vaporization of a chemical vapor deposition starting material, problems have occurred when the chemical vapor deposition starting material is heated to high temperatures, i.e., the film quality of the metal thin film has deteriorated and the electrical resistance has assumed high values and the desired electrical properties have not been obtained. Thus, there has been demand for chemical vapor deposition starting materials that can form metal thin films by undergoing thermal decomposition at low temperatures.

For example, when a metallic copper thin film is formed by vaporizing, for example, a chemical vapor deposition starting material, the problem has occurred that the metallic copper thin film yielded by heating to 200° C. or above ends up having high electrical resistance values. While the cause of this problem has not been determined, the hypothesis here is that, due to the heating to 200° C. or above, the copper particles present in the obtained thin film assume larger diameters and/or these particles undergo aggregation. Thus, with regard to chemical vapor deposition starting materials for the formation of metallic copper thin films, there has been demand for such a chemical vapor deposition starting material for the formation of metallic copper thin films that undergo thermal decomposition at below 200° C. The conventional alkoxide compounds have not been thoroughly satisfactory with regard to thermal stability.

Accordingly, an object of the present invention is to provide a novel alkoxide compound that does not undergo autoignition, that has a low melting point, that exhibits a satisfactory volatility, and that, for example, can undergo thermal decomposition at below 200° C. in the case of the cobalt alkoxide compound and the copper alkoxide compound and can undergo thermal decomposition at not more than 240° C. in the case of the nickel alkoxide compound. Additional objects of the present invention are to provide a thin film-forming starting material containing this alkoxide compound, to provide a thin film formation method that uses this thin film-forming starting material, and to provide a novel alcohol compound for producing the alkoxide compound.

Means for Solving the Problem

As a result of extensive investigations, the present inventors discovered that a special alkoxide compound can solve the problem identified above and thus achieved the present invention.

Thus, the present invention relates to an alkoxide compound represented by the following general formula (I), to a thin film-forming starting material that contains this alkoxide compound, and to a thin film formation method that uses this thin film-forming starting material.

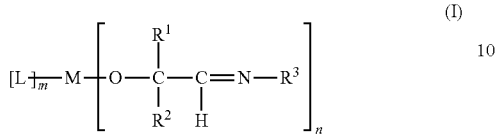
(I)

(In the formula, $R^1$ and $R^2$ each independently represent a hydrogen atom, a $C_{1-12}$ hydrocarbon group, or a group represented by any of the following general formulas (X-1) to (X-8). $R^3$ represents a hydrogen atom or a $C_{1-3}$ hydrocarbon group or a group represented by any of the following general formulas (X-1) to (X-8). However, when $R^1$ is a methyl group and $R^2$ is a methyl group or an ethyl group, $R^3$ represents a hydrogen atom or a group represented by any of the following general formulas (X-1) to (X-8). L represents a hydrogen atom, a halogen atom, a hydroxyl group, an amino group, an azido group, a phosphido group, a nitrile group, a carbonyl group, a $C_{1-12}$ hydrocarbon group, or a group represented by any of the following general formulas (L-1) to (L-13). M represents a metal atom or a silicon atom; n represents an integer equal to or greater than 1; m represents an integer equal to or greater than 0; and n+m represents the valence of the metal atom or silicon atom represented by M.)

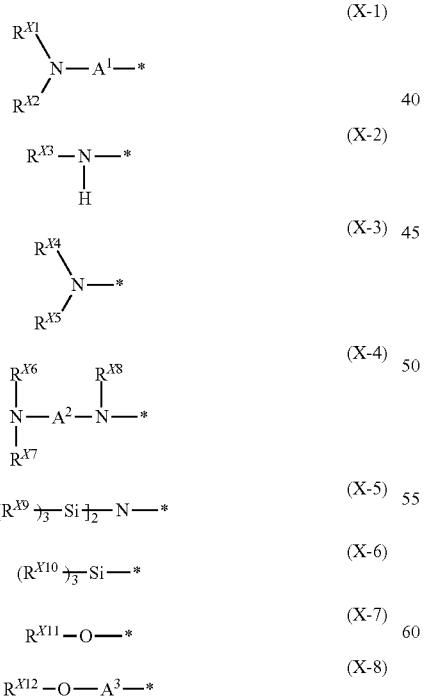

(In the formulas, $R^{X1}$ to $R^{X12}$ each independently represent a hydrogen atom or a $C_{1-12}$ hydrocarbon group, and $A^1$ to $A^3$ represent a $C_{1-6}$ alkanediyl group.)

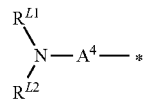 (L-1)

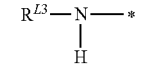 (L-2)

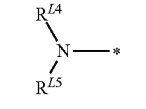 (L-3)

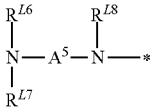 (L-4)

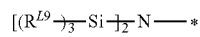 (L-5)

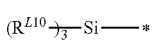 (L-6)

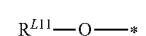 (L-7)

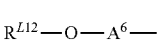 (L-8)

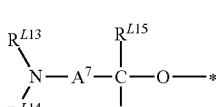 (L-9)

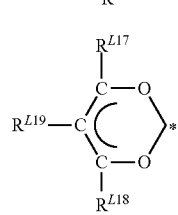 (L-10)

 (L-11)

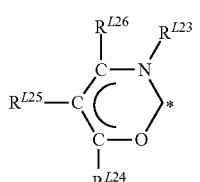 (L-12)

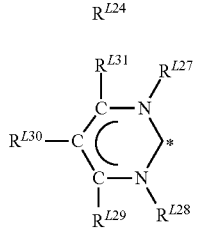 (L-13)

(In the formulas, $R^{L1}$ to $R^{L31}$ each independently represent a hydrogen atom or a $C_{1-12}$ hydrocarbon group and $A^4$ to $A^7$ represent a $C_{1-6}$ alkanediyl group. When an $R^{L1}$ to $R^{L31}$ is a $C_{1-12}$ hydrocarbon group, a hydrogen atom in the hydrocarbon group may be substituted by a halogen atom or an amino group.)

The present invention also relates to an alcohol compound represented by the following general formula (II).

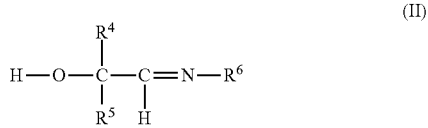

(II)

(In the formula, $R^4$ and $R^5$ each independently represent a hydrogen atom, a $C_{1-12}$ hydrocarbon group, or a group represented by any of the following general formulas (Y-1) to (Y-8). $R^6$ represents a hydrogen atom or a $C_{1-3}$ hydrocarbon group or a group represented by any of the following general formulas (Y-1) to (Y-8). However, when $R^4$ is a methyl group and $R^5$ is a methyl group or an ethyl group, $R^6$ represents hydrogen or a group represented by any of the following general formulas (Y-1) to (Y-8).

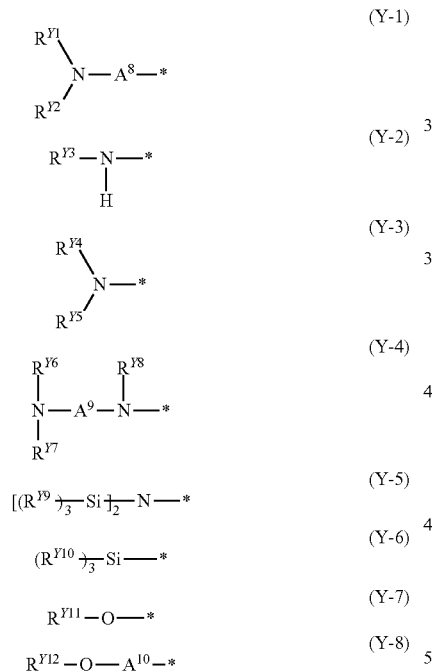

(In the formulas, $R^{Y1}$ to $R^{Y12}$ each independently represent a hydrogen atom or a $C_{1-12}$ hydrocarbon group, and $A^8$ to $A^{10}$ represent a $C_{1-6}$ alkanediyl group.)

Effects of the Invention

The present invention can provide an alkoxide compound that does not undergo autoignition, that has a low melting point, that exhibits a satisfactory volatility, and that, for example, can undergo thermal decomposition at below 200° C. in the case of the cobalt alkoxide compound and the copper alkoxide compound and can undergo thermal decomposition at not more than 240° C. in the case of the nickel alkoxide compound. This alkoxide compound is particularly suitable as a thin film-forming starting material for the formation of metal thin films by a CVD method. The present invention can also provide a novel alcohol compound.

BEST MODE FOR CARRYING OUT THE INVENTION

Figure 1:
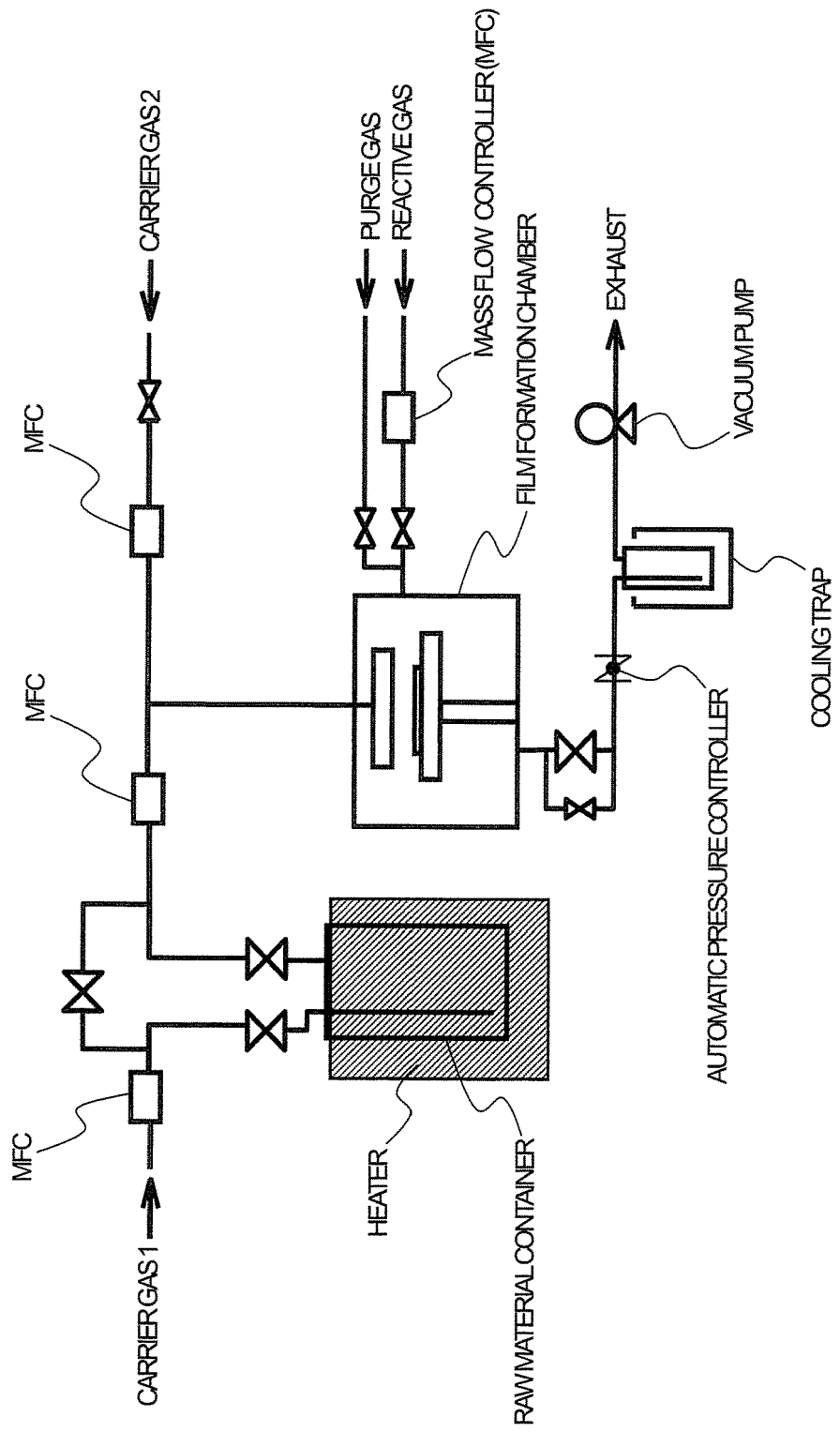
FIG. 1 is a schematic diagram that shows an example of a chemical vapor deposition apparatus used in the method according to the present invention for forming a metal-containing thin film.

The alkoxide compound of the present invention is represented by general formula (I); is highly suitable as a precursor in thin film production methods that have a vaporization step, e.g., a CVD method and so forth; and can also form a thin film using an ALD method. The alkoxide compound of the present invention has a low melting point and is a compound that becomes a liquid at 30° C. or when subjected to very minor heating. Since a compound having a low melting point has good transport characteristics, the alkoxide compound of the present invention is highly suitable as a precursor in thin film production methods that have a vaporization step, e.g., CVD methods and so forth.

$R^1$ and $R^2$ in general formula (I) of the present invention each independently represent a hydrogen atom, a $C_{1-12}$ hydrocarbon group, or a group represented by any of general formulas (X-1) to (X-8).

For example, alkyl, alkenyl, cycloalkyl, aryl, and cyclopentadienyl can be used as the $C_{1-12}$ hydrocarbon group represented by $R^1$ and $R^2$.

The alkyl can be exemplified by methyl, ethyl, propyl, isopropyl, butyl, isobutyl, sec-butyl, tert-butyl, pentyl, amyl, isoamyl, hexyl, heptyl, isoheptyl, octyl, isooctyl, 2-ethylhexyl, nonyl, isononyl, decyl, and dodecyl.

The alkenyl can be exemplified by vinyl, 1-methylethenyl, 2-methylethenyl, propenyl, butenyl, isobutenyl, pentenyl, hexenyl, heptenyl, octenyl, and decenyl.

The cycloalkyl can be exemplified by cyclohexyl, cyclopentyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

The aryl can be exemplified by phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tertiary-butylphenyl, 4-hexylphenyl, and 4-cyclohexylphenyl.

The cyclopentadienyl can be exemplified by cyclopentadienyl, methylcyclopentadienyl, ethylcyclopentadienyl, propylcyclopentadienyl, isopropylcyclopentadienyl, butylcyclopentadienyl, sec-butylcyclopentadienyl, isobutylcyclopentadienyl, tert-butylcyclopentadienyl, dimethylcyclopentadienyl, and tetramethylcyclopentadienyl.

$R^3$ in general formula (I) represents a hydrogen atom or a $C_{1-3}$ hydrocarbon group or a group represented by any of general formulas (X-1) to (X-8).

Specific examples of the $C_{1-3}$ hydrocarbon groups represented by $R^3$ are methyl, ethyl, propyl, isopropyl, vinyl, 1-methylethenyl, 2-methylethenyl, and propenyl.

In general formulas (X-1) to (X-8), the $R^{X1}$ to $R^{X12}$ each independently represent a hydrogen atom or a $C_{1-12}$ hydrocarbon group, and $A^1$ to $A^3$ represent a $C_{1-6}$ alkanediyl group.

The $C_{1-12}$ hydrocarbon groups represented by $R^{X1}$ to $R^{X12}$ can be specifically exemplified by the same groups as the groups provided as examples of the $C_{1-12}$ hydrocarbon groups represented by $R^1$ and $R^2$.

The $C_{1-6}$ alkanediyl groups represented by $A^1$ to $A^3$ can be exemplified by methylene, ethylene, propylene, and butylene.

The group represented by general formula (X-1) can be exemplified by dimethylaminomethyl, ethylmethylaminomethyl, diethylaminomethyl, dimethylaminoethyl, ethylmethylaminoethyl, and diethylaminoethyl.

The group represented by general formula (X-2) can be exemplified by methylamino, ethylamino, propylamino, isopropylamino, butylamino, sec-butylamino, tert-butylamino, and isobutylamino.

The group represented by general formula (X-3) can be exemplified by dimethylamino, diethylamino, dipropylamino, diisopropylamino, dibutylamino, di-sec-butylamino, di-tert-butylamino, ethylmethylamino, propylmethylamino, and isopropylmethylamino.

Compounds that contribute the group represented by general formula (X-4) can be exemplified by ethylenediamino, hexamethylenediamino, and N,N-dimethylethylenediamino.

The group represented by general formula (X-5) can be exemplified by di(trimethylsilyl)amino and di(triethylsilyl)amino.

The group represented by general formula (X-6) can be exemplified by trimethylsilyl and triethylsilyl.

The group represented by general formula (X-7) can be exemplified by methoxy, ethoxy, propoxy, isopropoxy, butoxy, sec-butoxy, isobutoxy, tert-butoxy, pentoxy, isopentoxy, and tert-pentoxy.

The group represented by general formula (X-8) can be exemplified by hydroxymethyl, hydroxyethyl, hydroxypropyl, hydroxyisopropyl, and hydroxybutyl.

In general formula (I), when $R^1$ is a methyl group and $R^2$ is a methyl group or an ethyl group, $R^3$ represents a hydrogen atom or a group represented by any of general formulas (X-1) to (X-8).

For the case in which thin film formation includes a step of vaporizing the alkoxide compound, the $R^1$, $R^2$, and $R^3$ in general formula (I) preferably provide a large vapor pressure and a low melting point. In the particular case of formation of a metal thin film, they preferably produce thermal decomposition at, for example, a temperature below 200° C. for the cobalt alkoxide compound and copper alkoxide compound and a temperature of not more than 240° C. for the nickel alkoxide compound. Specifically, $R^1$ and $R^2$ are preferably each independently a hydrogen atom, a $C_{1-12}$ hydrocarbon group, or a group represented by (X-5) because this provides a high vapor pressure, whereamong at least one of $R^1$ and $R^2$ is particularly preferably $C_{1-5}$ alkyl, di(trimethylsilyl)amino, or di(triethylsilyl)amino because this provides a low melting point. More particularly, $R^1$ and $R^2$ are preferably both ethyl for the low melting point this provides, and $R^1$, $R^2$, and $R^3$ are preferably all ethyl for the particularly low melting point this provides. In the case of a thin film production method using a MOD method, which is not accompanied by a vaporization step, $R^1$, $R^2$, and $R^3$ can be freely selected in accordance with the solubility in the solvent used, the thin film formation reaction, and so forth.

The L in general formula (I) of the present invention represents a hydrogen atom, a halogen, a hydroxyl group, an amino group, an azido group, a phosphido group, a nitrile group, a carbonyl group, a $C_{1-12}$ hydrocarbon group, or a group represented by any of general formulas (L-1) to (L-13). $R^{L1}$ to $R^{L31}$ in general formulas (L-1) to (L-13) each independently represent a hydrogen atom or a $C_{1-12}$ hydrocarbon group and $A^4$ to $A^7$ represent a $C_{1-6}$ alkanediyl group. When an $R^{L1}$ to $R^{L31}$ in general formulas (L-1) to (L-13) is a $C_{1-12}$ hydrocarbon group, a hydrogen atom in the hydrocarbon group may be substituted by a halogen atom or an amino group.

The $C_{1-12}$ hydrocarbon groups represented by $R^{L1}$ to $R^{L31}$ can be specifically exemplified by the same groups as the groups provided as examples of the $C_{1-12}$ hydrocarbon groups represented by $R^1$ and $R^2$.

The $C_{1-6}$ alkanediyl groups represented by $A^4$ to $A^7$ can be specifically exemplified by the same groups as the groups provided as examples of the $C_{1-6}$ alkanediyl groups represented by $A^1$ to $A^3$.

The group represented by general formula (L-1) can be exemplified by dimethylaminomethyl, ethylmethylaminomethyl, diethylaminomethyl, dimethylaminoethyl, ethylmethylaminoethyl, and diethylaminoethyl.

The group represented by general formula (L-2) can be exemplified by methylamino, ethylamino, propylamino, isopropylamino, butylamino, sec-butylamino, tert-butylamino, and isobutylamino.

The group represented by general formula (L-3) can be exemplified by dimethylamino, diethylamino, dipropylamino, diisopropylamino, dibutylamino, di-sec-butylamino, di-tert-butylamino, ethylmethylamino, propylmethylamino, and isopropylmethylamino.

Compounds that contribute the group represented by general formula (L-4) can be exemplified by ethylenediamino, hexamethylenediamino, and N,N-dimethylethylenediamino.

The group represented by general formula (L-5) can be exemplified by di(trimethylsilyl)amino and di(triethylsilyl)amino.

The group represented by general formula (L-6) can be exemplified by trimethylsilyl and triethylsilyl.

The group represented by general formula (L-7) can be exemplified by methoxy, ethoxy, propoxy, isopropoxy, butoxy, sec-butoxy, isobutoxy, tert-butoxy, pentoxy, isopentoxy, and tert-pentoxy.

The group represented by general formula (L-8) can be exemplified by hydroxymethyl, hydroxyethyl, hydroxypropyl, hydroxyisopropyl, and hydroxybutyl.

The group represented by general formula (L-9) can be exemplified by dimethylaminoethoxy, diethylaminoethoxy, dimethylaminopropoxy, ethylmethylaminopropoxy, and diethylaminopropoxy.

The group represented by general formula (L-10) can be exemplified by the groups represented by the following chemical formulas Nos. (L-10-1) to (L-10-5). In chemical formulas Nos. (L-10-1) to (L-10-5), "Me" represents methyl; "Et" represents ethyl; "iPr" represents isopropyl; and "tBu" represents tert-butyl.

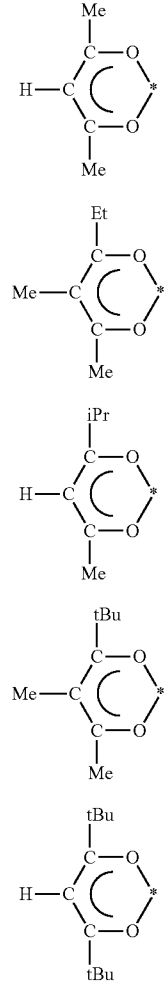

Organic compounds that provide the group represented by general formula (L-10) can be exemplified by the following: acetylacetone, hexane-2,4-dione, 5-methylhexane-2,4-dione, heptane-2,4-dione, 2-methylheptane-3,5-dione, 2,6-dimethylheptane-3,5-dione, 1,1,1-trifluoropentane-2,4-dione, 1,1,1-trifluoro-5,5-dimethylhexane-2,4-dione, 1,1,1,5,5,5-hexafluoropentane-2,4-dione, 1,3-diperfluorohexylpropane-1,3-dione, 1,1,5,5-tetramethyl-1-methoxyhexane-2,4-dione, 2,2,6,6-tetramethyl-1-methoxyheptane-3,5-dione, 2,2,6,6-tetramethyl-1-(2-methoxyethoxy)heptane-3,5-dione, 1,1,1-trifluoropentane-2,4-dione, 1,1,1-trifluoro-5,5-dimethylhexane-2,4-dione, 1,1,1,5,5,5-hexafluoropentane-2,4-dione, 1,3-diperfluorohexylpropane-1,3-dione, 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

The group represented by general formula (L-11) can be exemplified by the groups represented by the following chemical formulas Nos. (L-11-1) to (L-11-3). In chemical formulas Nos. (L-11-1) to (L-11-3), "Me" represents methyl; "iPr" represents isopropyl; and "tBu" represents tert-butyl.

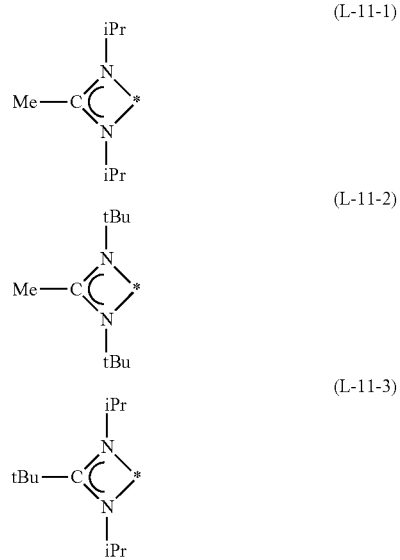

Organic compounds that provide the group represented by general formula (L-11) can be exemplified by N,N'-diisopropylacetamidinato, N,N'-di-t-butylacetamidinato, and N,N'-diisopropyl-2-t-butylamidinato.

The group represented by general formula (L-12) can be exemplified by the groups represented by the following chemical formulas Nos. (L-12-1) to (L-12-8). In chemical formulas Nos. (L-12-1) to (L-12-8), "Me" represents methyl; "iPr" represents isopropyl; and "tBu" represents tert-butyl.

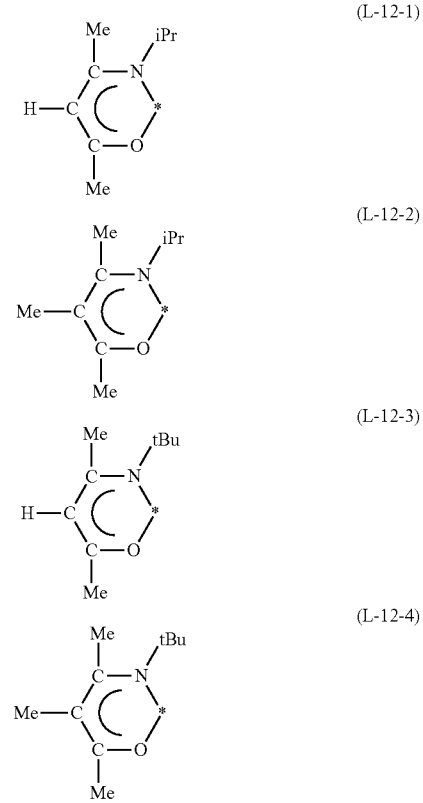

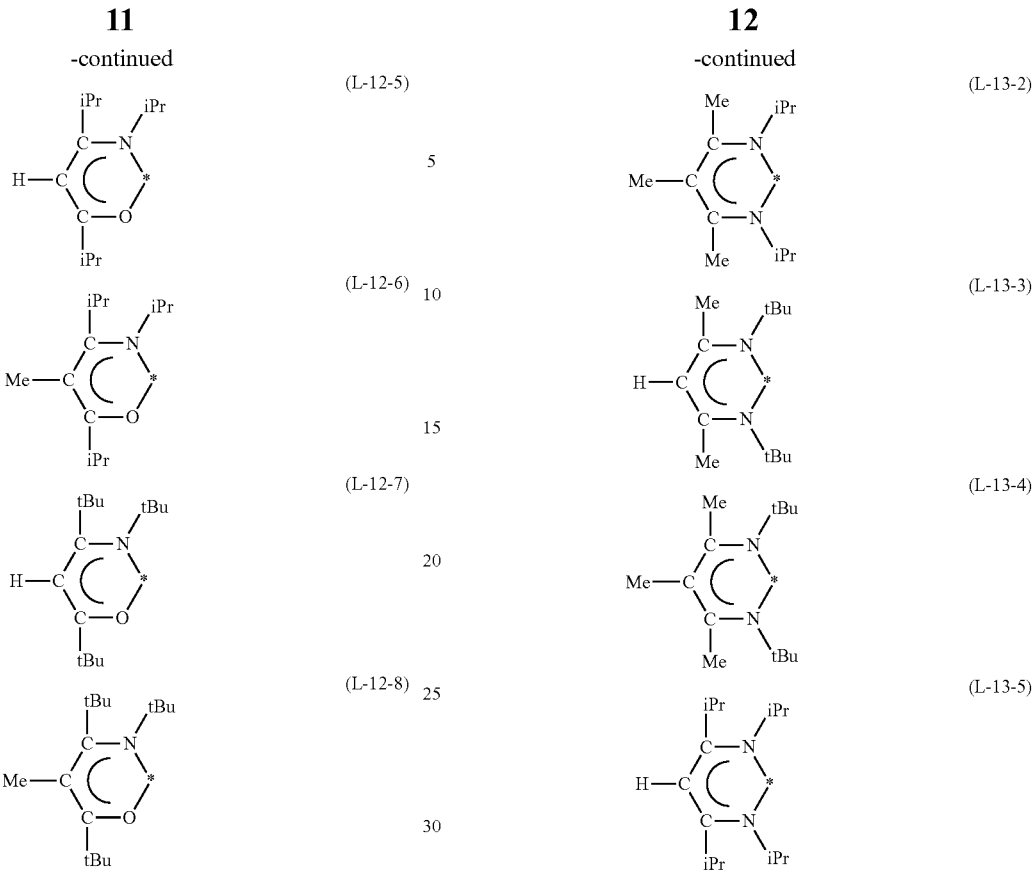

Organic compounds that provide the group represented by general formula (L-12) can be exemplified by the reaction product of an organic amine compound, as represented by methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, isopropylmethylamine, ethylenediamine, and N,N-dimethylethylenediamine, with a diketone compound, as represented by acetylacetone, hexane-2,4-dione, 5-methylhexane-2,4-dione, heptane-2,4-dione, 2-methylheptane-3,5-dione, 2,6-dimethylheptane-3,5-dione, 1,1,1-trifluoropentane-2,4-dione, 1,1,1-trifluoro-5,5-dimethylhexane-2,4-dione, 1,1,1,5,5,5-hexafluoropentane-2,4-dione, 1,3-diperfluorohexylpropane-1,3-dione, 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

The group represented by general formula (L-13) can be exemplified by the groups represented by the following chemical formulas Nos. (L-13-1) to (L-13-8). In chemical formulas Nos. (L-13-1) to (L-13-8), "Me" represents methyl; "iPr" represents isopropyl; and "tBu" represents tert-butyl.

[Chemical Formula 9]

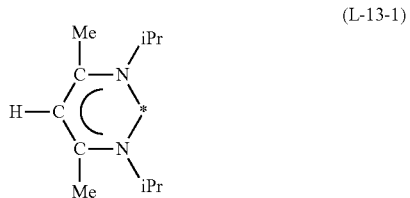

Organic compounds that provide the group represented by general formula (L-13) can be exemplified by N-isopropyl-4-(isopropylimino)pent-2-en-2-amine, N-isopropyl-4-(isopropylimino)-3-methylpent-2-en-2-amine, N-(tert-butyl)-4-(tert-butylimino)pent-2-en-2-amine, N-(tert-butyl)-4-(tert-butylimino)-3-methylpent-2-en-2-amine, N-isopropyl-5-(isopropylimino)-2,6-dimethylhept-3-en-3-amine, N-isopropyl-5-(isopropylimino)-2,4,6-trimethylhept-3-en-3-amine, N-(tert-butyl)-5-(tert-butylimino)-2,2,6,6-tetramethylhept-3-en-3-amine, and N-(tert-butyl)-5-(tert-butylimino)-2,2,4,6,6-pentamethylhept-3-en-3-amine.

It is particularly preferred for m in general formula (I) to be equal to or greater than 1 and for L to be a group represented by (L-11) and/or a cyclopentadienyl group as typified by cyclopentadienyl, methylcyclopentadienyl, ethylcyclopentadienyl, and pentamethylcyclopentadienyl, because this provides a high thermal stability and a higher vapor pressure. In addition, when m in general formula (I) of the present invention is equal to or greater than 2, the L's may be the same as each other or may differ from one another.

The M in general formula (I) is a metal atom or a silicon atom. This metal atom is not particularly limited and can be exemplified by lithium, sodium, potassium, magnesium, calcium, strontium, barium, radium, scandium, yttrium, titanium, zirconium, hafnium, vanadium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium. Among the preceding, M is particularly preferably copper, iron, nickel, cobalt, or manganese because this provides a particularly high thermal stability.

In general formula (I) of the present invention, n represents an integer equal to or greater than 1; m represents an integer equal to or greater than 0; and n+m represents the valence of the metal atom or silicon atom represented by M.

The alkoxide compound represented by general formula (I) may in some cases exhibit optical activity; however, the alkoxide compound of the present invention is not particularly distinguished with regard to the (R)-compound and (S)-compound and may be either or may be a mixture of the (R)-compound and (S)-compound in any proportions. The racemic mixture has low production costs.

The following general formula (I-A) represents the case in which the alkoxide compound of the present invention forms a cyclic structure through the coordination of terminal donor groups in the ligand to the metal atom or silicon atom. Here, the alkoxide compound of the present invention, while being represented by general formula (I), is not to be differentiated from the alkoxide compound represented by general formula (I-A) and also encompasses the alkoxide compound represented by general formula (I-A).

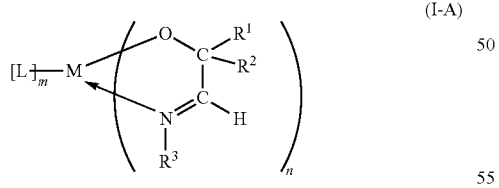

(I-A)

(In the formula, $R^1$ and $R^2$ each independently represent a hydrogen atom, a $C_{1-12}$ hydrocarbon group, or a group represented by any of the following general formulas (X-1) to (X-8). $R^3$ represents a hydrogen atom or a $C_{1-3}$ hydrocarbon group or a group represented by any of the following general formulas (X-1) to (X-8). However, when $R^1$ is a methyl group and $R^2$ is a methyl group or an ethyl group, $R^3$ represents a hydrogen atom or a group represented by any of the following general formulas (X-1) to (X-8). L represents a hydrogen atom, halogen, a hydroxyl group, an amino group, an azido group, a phosphido group, a nitrile group, a carbonyl group, a $C_{1-12}$ hydrocarbon group, or a group represented by any of the following general formulas (L-1) to (L-13). M represents a metal atom or a silicon atom; n represents an integer equal to or greater than 1; m represents an integer equal to or greater than 0; and n+m represents the valence of the metal atom or silicon atom represented by M.)

(X-1)

(X-2)

(X-3)

(X-4)

(X-5)

(X-6)

(X-7)

(X-8)

(In the formulas, $R^{X1}$ to $R^{X12}$ each independently represent a hydrogen atom or a $C_{1-12}$ hydrocarbon group, and $A^1$ to $A^3$ represent a $C_{1-6}$ alkanediyl group.)

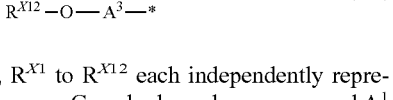

(L-1)

(L-2)

(L-3)

(L-4)

(L-5)

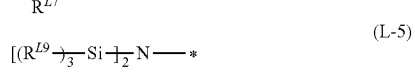

(L-6)

(L-7)

(L-8)

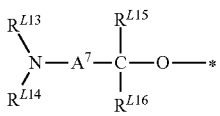
(L-9)

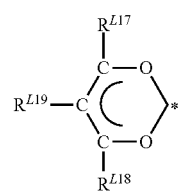
(L-10)

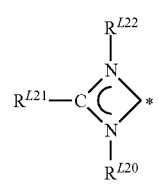
(L-11)

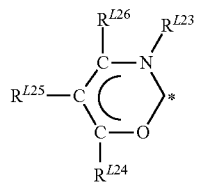
(L-12)

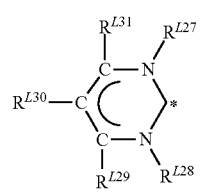
(L-13)

(In the formulas, $R^{L1}$ to $R^{L31}$ each independently represent hydrogen or a $C_{1\text{-}12}$ hydrocarbon group and $A^4$ to $A^7$ represent a $C_{1\text{-}6}$ alkanediyl group. When an $R^{L1}$ to $R^{L31}$ is a $C_{1\text{-}12}$ hydrocarbon group, a hydrogen atom in the hydrocarbon group may be substituted by a halogen atom or an amino group.)

Preferred specific examples of the alkoxide compound represented by general formula (I) are, for example, the compounds represented by the following chemical formulas No. 1 to No. 91 when M=cobalt. In chemical formulas No. 1 to No. 91, "Me" represents methyl; "Et" represents ethyl; "iPr" represents isopropyl; "Cp" represents cyclopentadienyl; "MeCp" represents methylcyclopentadienyl; "sCp" represents pentamethylcyclopentadienyl; and "AMD" represents N, N'-diisopropylacetamidinato.

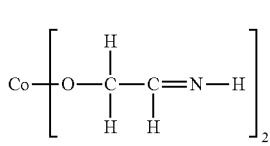
No.1

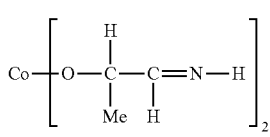
No.2

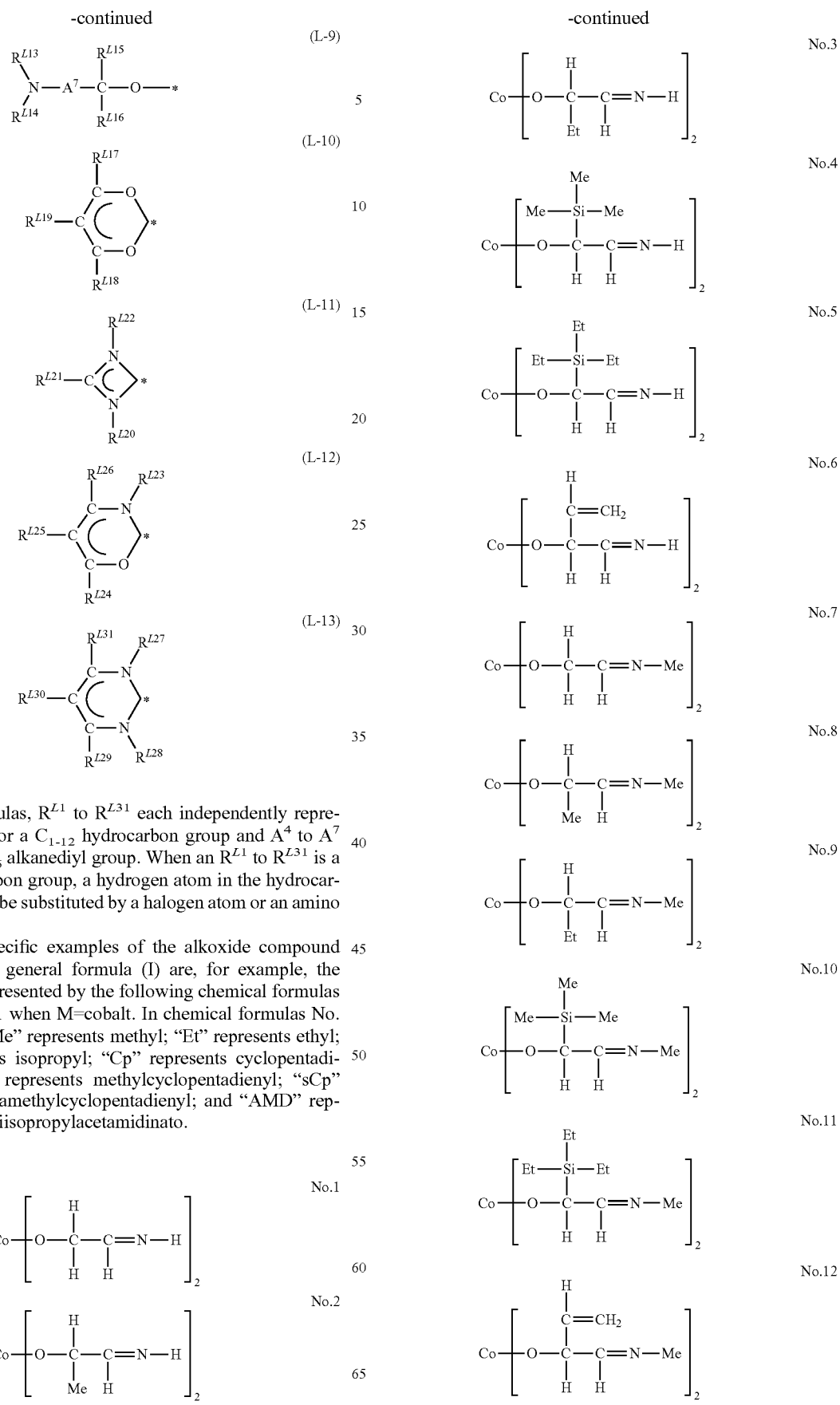

-continued

No.13

Co―[O―CH(H)―C(H)=N―Et]₂

No.14

Co―[O―C(Me)(H)―C(H)=N―Et]₂

No.15

Co―[O―C(Et)(H)―C(H)=N―Et]₂

No.16

Co―[O―C(SiMe₃)(H)―C(H)=N―Et]₂

No.17

Co―[O―C(SiEt₃)(H)―C(H)=N―Et]₂

No.18

Co―[O―C(CH=CH₂)(H)―C(H)=N―Et]₂

No.19

Co―[O―C(H)(H)―C(H)=N―iPr]₂

No.20

Co―[O―C(Me)(H)―C(H)=N―iPr]₂

No.22

Co―[O―C(SiMe₃)(H)―C(H)=N―iPr]₂

No.23

Co―[O―C(SiEt₃)(H)―C(H)=N―iPr]₂

No.24

Co―[O―C(CH=CH₂)(H)―C(H)=N―iPr]₂

No.25

Co―[O―C(H)(H)―C(H)=N―NMe₂]₂

No.26

Co―[O―C(Me)(H)―C(H)=N―NMe₂]₂

No.27

Co―[O―C(Et)(H)―C(H)=N―NMe₂]₂

No.28

Co―[O―C(SiMe₃)(H)―C(H)=N―NMe₂]₂

No.29

Co―[O―C(SiEt₃)(H)―C(H)=N―NMe₂]₂

No.30

Co―[O―C(CH=CH₂)(H)―C(H)=N―NMe₂]₂

No.31

Co―[O―C(H)(H)―C(H)=N―SiMe₃]₂

No.32

Co―[O―C(Me)(H)―C(H)=N―SiMe₃]₂

No.33

Co―[O―C(Et)(H)―C(H)=N―SiMe₃]₂

-continued
No.34
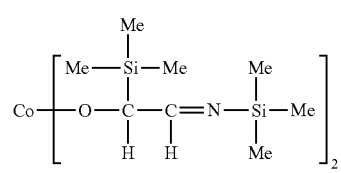
No.35
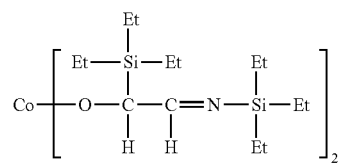
No.36
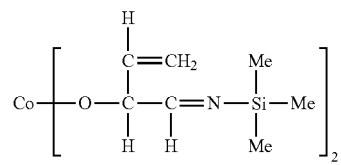
No.37
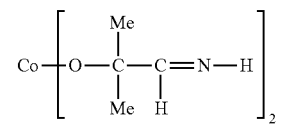
No.38
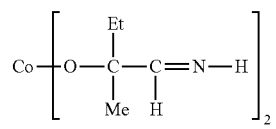
No.39
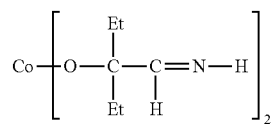
No.40
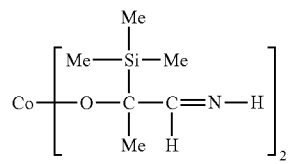
No.41
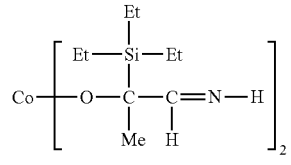
No.42
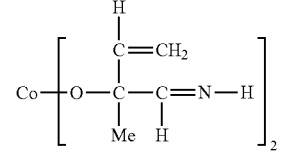
No.43
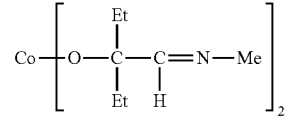
-continued
No.44
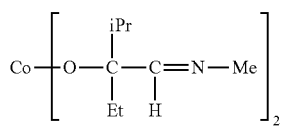
No.45
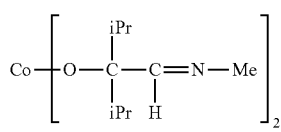
No.46
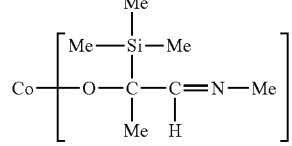
No.47
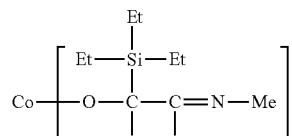
No.48
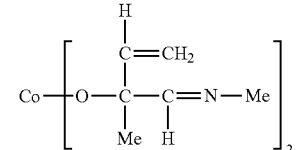
No.49
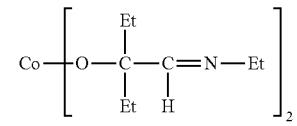
No.50
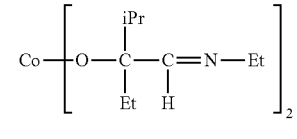
No.51
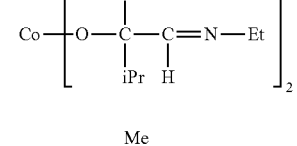
No.52
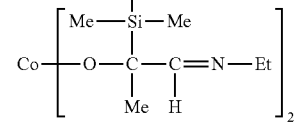
No.53
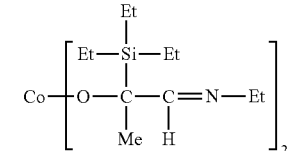

No. 54 – No. 73: cobalt complex structures (chemical diagrams).

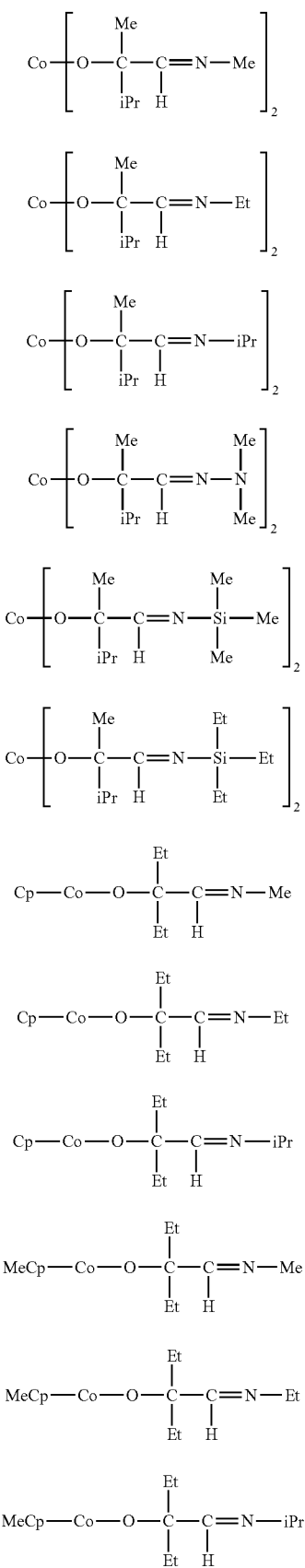
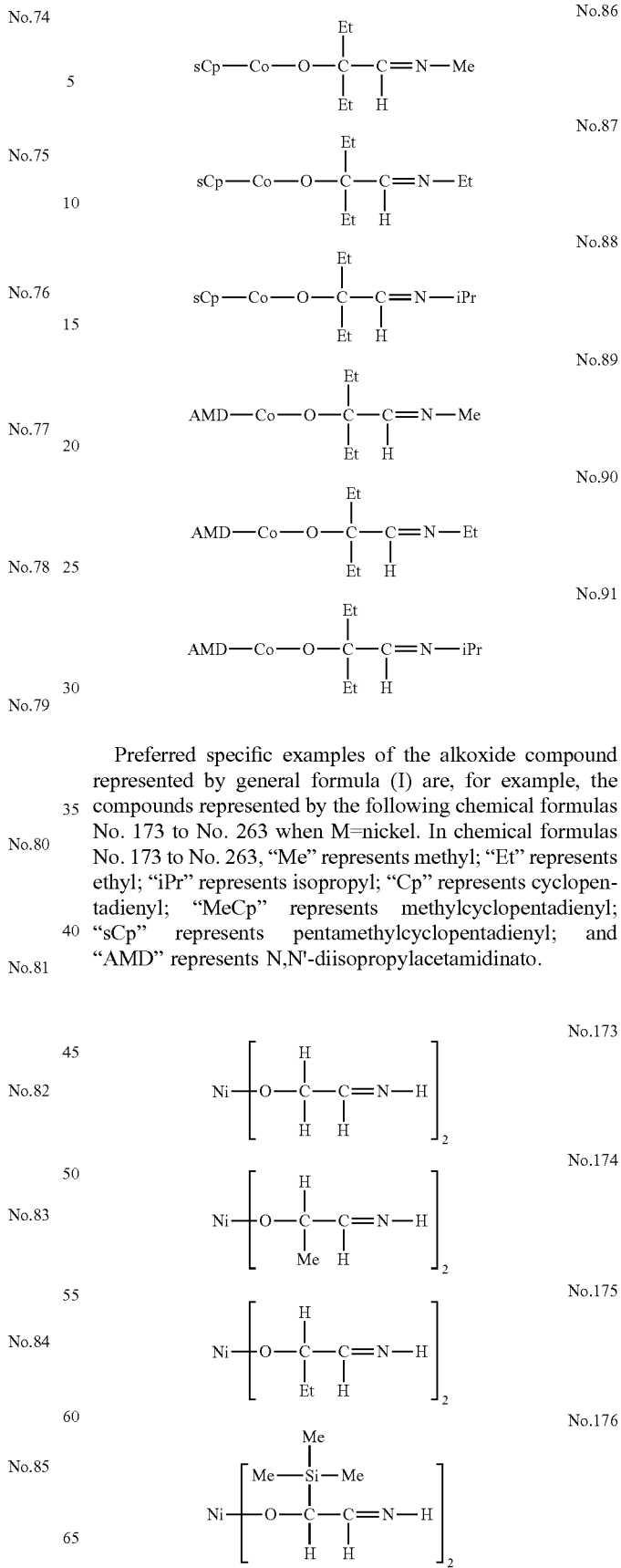

Preferred specific examples of the alkoxide compound represented by general formula (I) are, for example, the compounds represented by the following chemical formulas No. 173 to No. 263 when M=nickel. In chemical formulas No. 173 to No. 263, "Me" represents methyl; "Et" represents ethyl; "iPr" represents isopropyl; "Cp" represents cyclopentadienyl; "MeCp" represents methylcyclopentadienyl; "sCp" represents pentamethylcyclopentadienyl; and "AMD" represents N,N'-diisopropylacetamidinato.

No.177 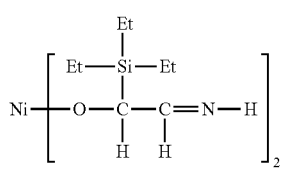
No.178 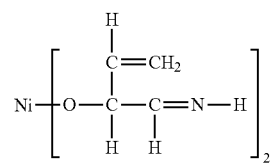
No.179 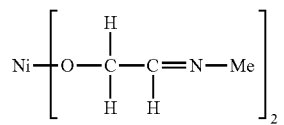
No.180 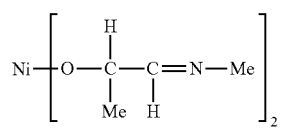
No.181 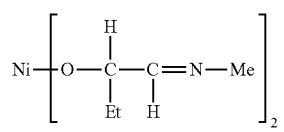
No.182 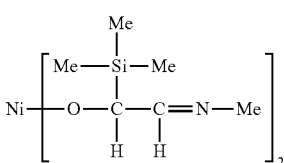
No.183 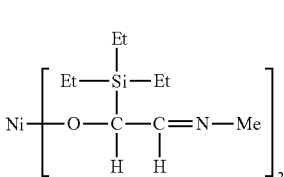
No.184 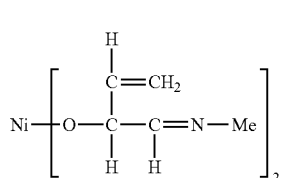
No.185 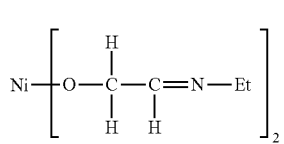
No.186 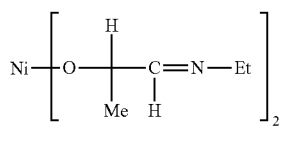
No.187 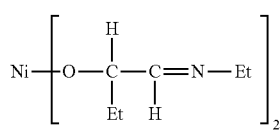
No.188 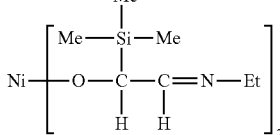
No.189 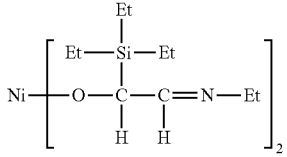
No.190 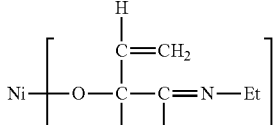
No.191 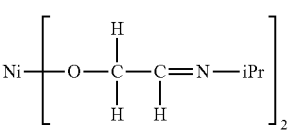
No.192 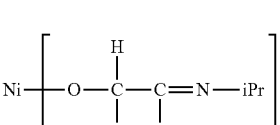
No.193 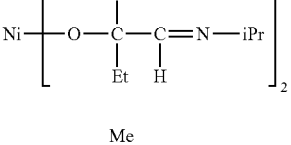
No.194 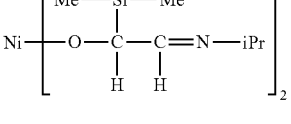
No.195 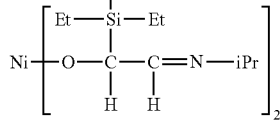
No.196 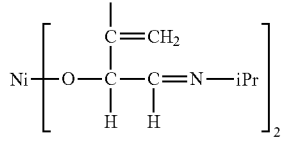

-continued

No.197

Ni—[O—CH₂—CH=N—N(Me)₂]₂

No.198

Ni—[O—CH₂—CH=N—N(Me)₂]₂

No.199

Ni—[O—CH(Et)—CH=N—N(Me)₂]₂

No.200

Ni—[O—C(SiMe₃)H—CH=N—N(Me)₂]₂

No.201

Ni—[O—C(SiEt₃)H—CH=N—N(Me)₂]₂

No.202

Ni—[O—C(C(=CH₂)H)H—CH=N—N(Me)₂]₂

No.203

Ni—[O—CH₂—CH=N—SiMe₃]₂

No.204

Ni—[O—CH(Me)—CH=N—SiMe₃]₂

No.205

Ni—[O—CH(Et)—CH=N—SiMe₃]₂

No.206

Ni—[O—C(SiMe₃)H—CH=N—SiMe₃]₂

-continued

No.207

Ni—[O—C(SiEt₃)H—CH=N—SiEt₃]₂

No.208

Ni—[O—C(C(=CH₂)H)H—CH=N—Si(Me)(Et)₂]₂

No.209

Ni—[O—C(Me)₂—CH=N—H]₂

No.210

Ni—[O—C(Me)(H)—CH=N—H]₂

No.211

Ni—[O—C(Et)(H)—CH=N—H]₂

No.212

Ni—[O—C(SiMe₃)(Et)—CH=N—H]₂

No.213

Ni—[O—C(SiEt₃)(Et)—CH=N—H]₂

No.214

Ni—[O—C(C(=CH₂)H)(Me)—CH=N—H]₂

No.215

Ni—[O—C(Et)(Et)—CH=N—Me]₂

No.216

Ni—[O—C(iPr)(Et)—CH=N—Me]₂

No.217 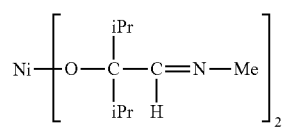
No.218 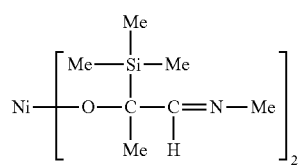
No.219 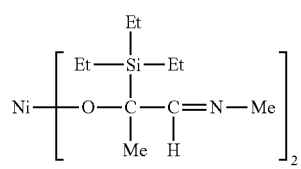
No.220 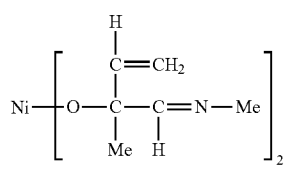
No.221 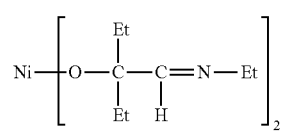
No.222 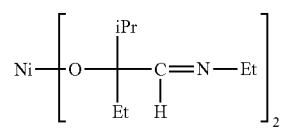
No.223 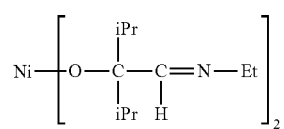
No.224 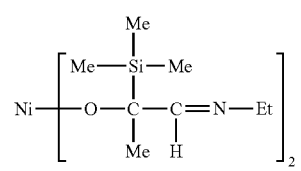
No.225 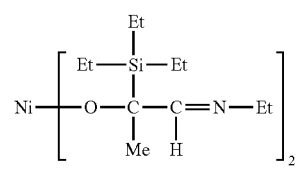
No.226 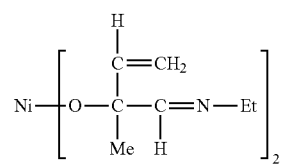
No.227 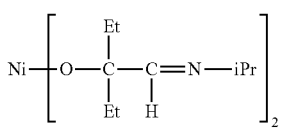
No.228 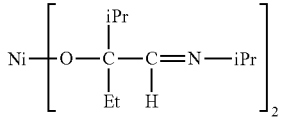
No.229 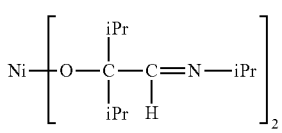
No.230 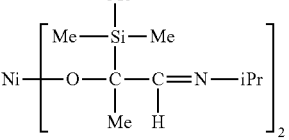
No.231 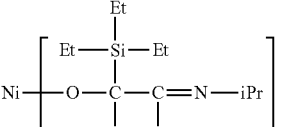
No.232 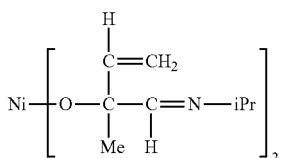
No.233 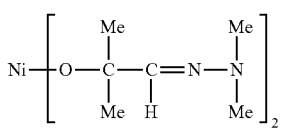
No.234 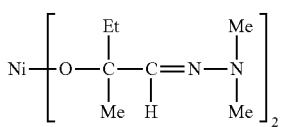
No.235 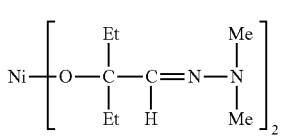
No.236 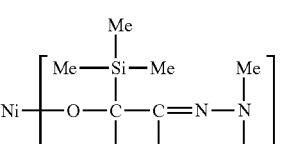

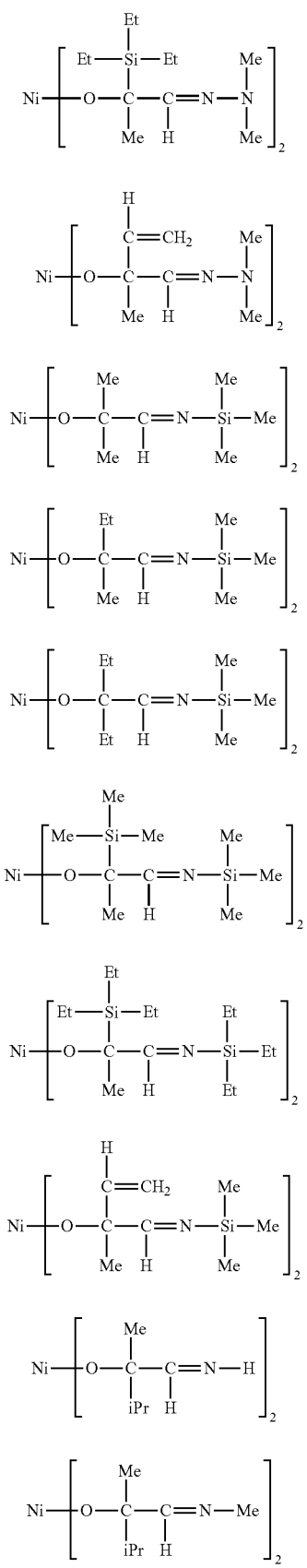
No.237
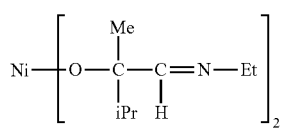
No.247
No.238
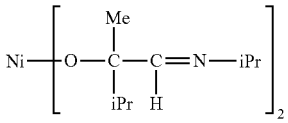
No.248
No.239
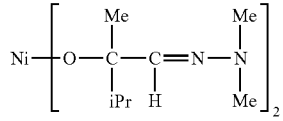
No.249
No.240
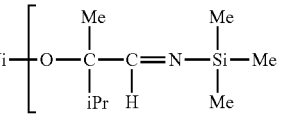
No.250
No.241
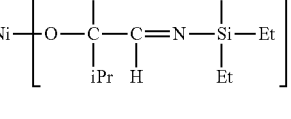
No.251
No.242
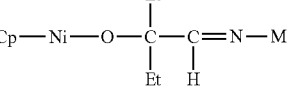
No.252
No.243
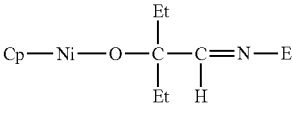
No.253
No.244
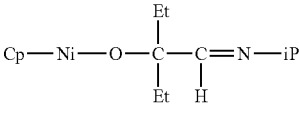
No.254
No.245
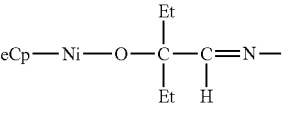
No.255
No.246
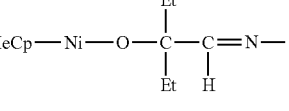
No.256
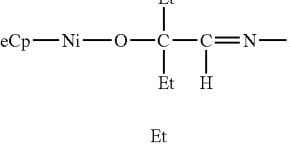
No.257
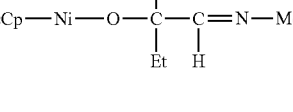
No.258

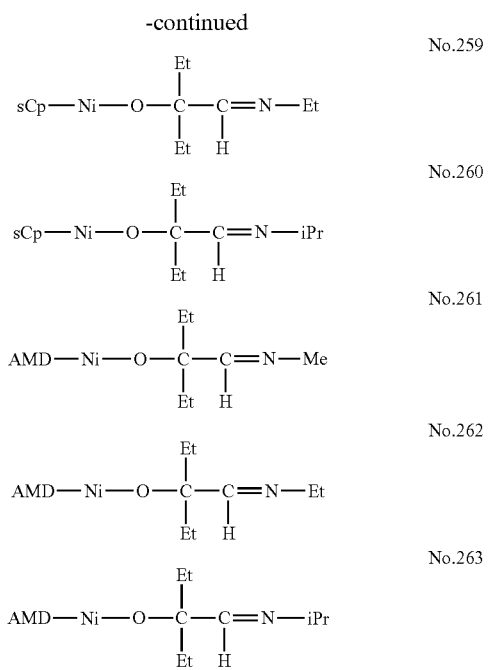

The alkoxide compound of the present invention is not particularly limited with regard to its method of production, and it can be produced by the application of known reactions. Commonly known methods for the synthesis of alkoxide compounds using the corresponding alcohol can be applied as the method of producing the alkoxide compound represented by general formula (I) in which m=0, for example, as follows for production of the cobalt alkoxide compound: methods in which an inorganic salt of cobalt, e.g., the halide or nitrate salt, or a hydrate thereof is reacted with the corresponding alcohol compound in the presence of a base such as sodium, sodium hydride, sodium amide, sodium hydroxide, sodium methylate, ammonia, an amine, and so forth; methods in which an inorganic salt of cobalt, e.g., the halide or nitrate salt, or a hydrate thereof is reacted with the alkali metal alkoxide of the corresponding alcohol compound, e.g., the sodium alkoxide, lithium alkoxide, potassium alkoxide, and so forth; methods in which an exchange reaction is run between the corresponding alcohol compound and an alkoxide compound of cobalt with a low molecular weight alcohol, e.g., the methoxide, ethoxide, isopropoxide, butoxide, and so forth; and methods in which an inorganic salt of cobalt, e.g., the halide or nitrate salt, is reacted with a derivative that provides a reactive intermediate to obtain a reactive intermediate and this is then reacted with the corresponding alcohol compound. The reactive intermediate can be exemplified by bis(dialkylamino)cobalt, bis(bis(trimethylsilyl)amino)cobalt, and amide compounds of cobalt. The method of producing the alkoxide compound in which m in general formula (I) is equal to or greater than 1 can be exemplified by methods in which the alkoxide compound for which m=0 in general formula (I) is produced by a production method as described above followed by reaction with an organic compound that contributes the desired ligand or with the alkali metal salt of such an organic compound.

The thin film-forming starting material of the present invention employs the above-described alkoxide compound of the present invention as a thin film precursor, and its formulation will vary as a function of the production process in which the thin film-forming starting material is applied. For example, when a thin film containing only silicon or a single species of metal is to be produced, the thin film-forming starting material of the present invention will not contain a metal compound or semimetal compound other than the alkoxide compound. When, on the other hand, a thin film containing two or more species of metal and/or semimetal is to be produced, the thin film-forming starting material of the present invention will contain, in addition to the alkoxide compound, a compound containing the desired metal and/or a compound containing the desired semimetal (also referred to hereafter as the additional precursor). The thin film-forming starting material of the present invention may, as described below, additionally contain an organic solvent and/or a nucleophilic reagent. Because, as has been described above, the properties of the precursor alkoxide compound are well suited to the CVD and ALD methods, the thin film-forming starting material of the present invention is thus particularly useful as a chemical vapor deposition starting material (also referred to hereafter as a CVD starting material).

When the thin film-forming starting material of the present invention is a chemical vapor deposition starting material, its formulation is selected as appropriate as a function of the techniques, e.g., the transport and supply procedures and so forth, in the CVD method that is used.

This transport and supply procedure can be a gas transport method or a liquid transport method: in the former, the CVD starting material residing in a container that stores the starting material (also referred to hereafter simply as a starting material container) is vaporized into vapor by heating and/or reducing the pressure and this vapor is introduced, in combination with a carrier gas used on an optional basis, e.g., argon, nitrogen, helium, and so forth, into a film-formation chamber in which the substrate is disposed (also referred to hereafter as the deposition reaction section); in the latter, the CVD starting material is transported in a liquid or solution state to a vaporizer and is vaporized into a vapor at the vaporizer by heating and/or reducing the pressure and this vapor is then introduced into the film-formation chamber. In the gas transport method, the alkoxide compound represented by general formula (I) can itself be used as the CVD starting material. In the liquid transport method, the alkoxide compound represented by general formula (I) itself or a solution provided by dissolving this compound in an organic solvent can be used as the CVD starting material. These CVD starting materials may also contain an additional precursor, a nucleophilic reagent, and so forth.

In addition, the CVD method with a multicomponent system includes a method in which each component of the CVD starting material is independently vaporized and supplied (also referred to herebelow as the single-source method) and a method in which a starting material mixture, prepared by preliminarily mixing the multicomponent starting material in the desired composition, is vaporized and supplied (also referred to herebelow as the cocktail-source method). In the case of the cocktail-source method, the CVD starting material can be a mixture of the alkoxide compound of the present invention and an additional precursor or can be a mixed solution provided by dissolving such a mixture in an organic solvent. This mixture or mixed solution can additionally contain, for example, a nucleophilic reagent. When only the alkoxide compound of the present invention is used as the precursor and a combination of (R)-compound and (S)-compound is used, a CVD starting material containing the (R)-compound may be vaporized separately from a CVD starting material containing the (S)-compound or a CVD starting material containing a mixture of the (R)-compound and (S)-compound may be vaporized.

There are no particular limitations on the organic solvent here, and commonly known organic solvents can be used. This organic solvent can be exemplified by acetate esters such as ethyl acetate, butyl acetate, and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; cyano group-containing hydrocarbons such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; and pyridine and lutidine. A single one of these solvents or a mixed solvent of two or more is used based on considerations such as the solubility of the solutes, the relationship between the use temperature and the boiling point and flash point, and so forth. When an organic solvent is used, the total amount of the precursor in the CVD starting material, which in this case is the solution provided by the dissolution of the precursor in the organic solvent, is preferably 0.01 to 2.0 mol/liter and is particularly preferably 0.05 to 1.0 mol/liter. Here, "the total amount of the precursor" is the amount of the alkoxide compound of the present invention when the thin film-forming starting material of the present invention does not contain a metal compound or semimetal compound other than the alkoxide compound of the present invention, and is the sum total amount of the alkoxide compound of the present invention and the additional precursor when the thin film-forming starting material of the present invention contains another metal-containing compound and/or semimetal-containing compound in addition to the alkoxide compound.

In the case of the CVD method with a multicomponent system, there are no particular limitations on the additional precursor used in combination with the alkoxide compound of the present invention, and the commonly known precursors used in CVD starting materials can be used.

This additional precursor can be exemplified by one or two or more compounds of silicon and/or a metal, selected from the group consisting of compounds having, for example, the following as a ligand: hydride, hydroxide, halide, azido, alkyl, alkenyl, cycloalkyl, aryl, alkynyl, amino, dialkylaminoalkyl, monoalkylamino, dialkylamino, diamine, di(silylalkyl)amino, di(alkylsilyl)amino, disilylamino, alkoxy, alkoxyalkyl, hydrazido, phosphido, nitrile, dialkylaminoalkoxy, alkoxyalkyldialkylamino, siloxy, diketonato, cyclopentadienyl, silyl, pyrazolato, guanidinato, phosphoguanidinato, amidinato, phosphoamidinato, ketoiminato, diketiminato, carbonyl, and phosphoamidinato.

The metal species in the precursor can be exemplified by magnesium, calcium, strontium, barium, radium, scandium, yttrium, titanium, zirconium, hafnium, vanadium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium.

These additional precursors are known in this technical field, and their production methods are also known. In an example of a production method, and taking the use of an alcohol compound for the organic ligand as an example, the precursor can be produced by reacting the alkali metal alkoxide of the alcohol compound with an inorganic salt of the metal, or a hydrate thereof. Here, the inorganic salt of the metal or hydrate thereof can be exemplified by the halide, nitrate salt, and so forth of the metal, and the alkali metal alkoxide can be exemplified by the sodium alkoxide, lithium alkoxide, and potassium alkoxide.

In the case of the single-source method, this additional precursor preferably is a compound that exhibits a thermal and/or oxidative decomposition behavior similar to that of the alkoxide compound of the present invention. In the case of the cocktail-source method, the additional precursor preferably has a similar thermal and/or oxidative decomposition behavior while also not undergoing alteration, e.g., by a chemical reaction, when mixed.

Among the additional precursors described above, precursors containing titanium, zirconium, or hafnium can be exemplified by compounds represented by the following formulas (II-1) to (II-5).

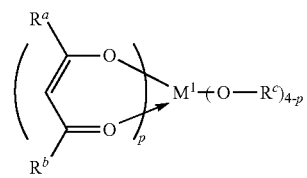

(II-1)

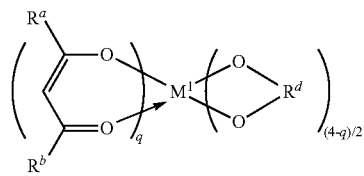

(II-2)

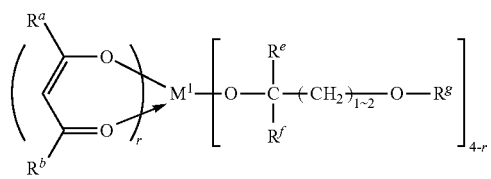

(II-3)

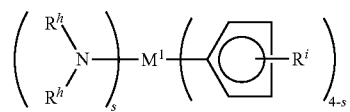

(II-4)

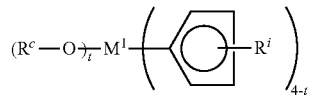

(II-5)

(In the formulas, $M^1$ represents titanium, zirconium, or hafnium; $R^a$ and $R^b$ each independently represent a $C_{1-20}$ alkyl group, which may be substituted by a halogen atom and which may contain an oxygen atom in the chain; $R^c$ represents a $C_{1-8}$ alkyl group; $R^d$ represents a possibly branched $C_{2-18}$ alkylene group; $R^e$ and $R^f$ each independently represent a hydrogen atom or a $C_{1-3}$ alkyl group; $R^g$, $R^h$, $R^k$, and $R^j$ each independently represent a hydrogen atom or a $C_{1-4}$ alkyl group; p represents an integer from 0 to 4; q represents 0 or 2; r represents an integer from 0 to 3; s represents an integer from 0 to 4; and t represents an integer from 1 to 4.)

The alkyl group represented by $R^a$ and $R^b$ in formulas (II-1) to (II-5) can be exemplified by methyl, ethyl, propyl, isopropyl, butyl, sec-butyl, tert-butyl, isobutyl, amyl, isoamyl, sec-amyl, tert-amyl, hexyl, cyclohexyl, 1-methylcyclohexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, and 2-(2-methoxyethoxy)-1,1-dimethylethyl. The alkyl group represented by $R^c$ can be exemplified by methyl, ethyl, propyl, isopropyl, butyl, sec-butyl, tert-butyl, isobutyl, amyl, isoamyl, sec-amyl, tert-amyl, hexyl, 1-ethylpentyl, cyclohexyl, 1-methylcyclohexyl, heptyl, isoheptyl, tert-heptyl, n-octyl, isooctyl, tert-octyl, and 2-ethylhexyl. The alkylene group represented by $R^d$ is a group provided by a glycol, and this glycol can be exemplified by 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. The alkyl group represented by $R^e$ and $R^f$ can be exemplified by methyl, ethyl, propyl, and 2-propyl, and the alkyl group represented by $R^g$, $R^h$, $R^j$, and $R^k$ can be exemplified by methyl, ethyl, propyl, isopropyl, butyl, sec-butyl, tert-butyl, and isobutyl.

The titanium-containing precursor can be specifically exemplified by tetrakisalkoxytitaniums such as tetrakis(ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-amyl)titanium, and tetrakis(1-methoxy-2-methyl-2-propoxy)titanium; tetrakis-β-diketonatotitaniums such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato) titaniums such as bis(methoxy)bis(pentane-2,4-dionato) titanium, bis(ethoxy)bis(pentane-2,4-dionato)titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato) titanium, bis(tert-amyloxy)bis(2,6-dimethylheptane-3,5-dionato)titanium, bis(methoxy)bis(2,2,6,6-tetramethylheptane-3,5-dionato) titanium, bis(ethoxy)bis(2,2,6,6-tetramethylheptane-3,5-dionato)titanium, bis(2-propoxy)bis(2,6,6,6-tetramethylheptane 3,5-dionato) titanium, bis(tert-butoxy)bis(2,2,6,6-tetramethylheptane-3,5-dionato)titanium, and bis(tert-amyloxy)bis(2,2,6,6-tetramethylheptane-3,5-dionato) titanium; glycoxybis(β-diketonato)titaniums such as (2-methylpentanedioxy)bis(2,2,6,6-tetramethylheptane-3,5-dionato)titanium and (2-methylpentanedioxy)bis(2,6-dimethylheptane-3,5-dionato) titanium; (cyclopentadienyl)tris(dialkylamino)titaniums such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino) titanium, (ethylcyclopentadienyl)tris(diethylamino) titanium, and (cyclopentadienyl)tris(diethylamino) titanium; and (cyclopentadienyl)tris(alkoxy)titaniums such as (cyclopentadienyl)tris(methoxy) titanium, (methylcyclopentadienyl)tris(methoxy) titanium, (ethylcyclopentadienyl)tris(methoxy) titanium, (propylcyclopentadienyl)tris(methoxy)titanium, (isopropylcyclopentadienyl)tris(methoxy)titanium, (butylcyclopentadienyl)tris(methoxy) titanium, (isobutylcyclopentadienyl)tris(methoxy)titanium, tert-butylcyclopentadienyl)tris (methoxy) titanium, and (pentamethylcyclopentadienyl)tris (methoxy)titanium. The zirconium-containing precursor and the hafnium-containing precursor can be exemplified by compounds provided by substituting zirconium or hafnium for the titanium in the compounds provided above as examples of the titanium-containing precursor.

Rare earth element-containing precursors can be exemplified by compounds represented by the following formulas (III-1) to (III-3).

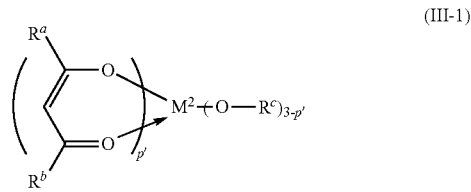

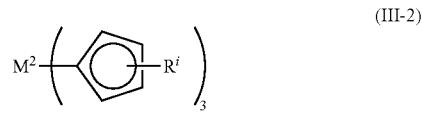

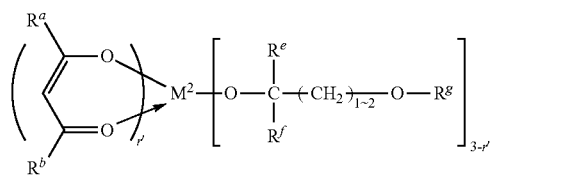

(In the formulas, $M^2$ represents a rare earth atom; $R^a$ and $R^b$ each independently represent a $C_{1-20}$ alkyl group, which may be substituted by a halogen atom and which may contain an oxygen atom in the chain; $R^c$ represents a $C_{1-8}$ alkyl group; $R^e$ and $R^f$ each independently represent a hydrogen atom or a $C_{1-3}$ alkyl group; $R^g$ and $R^j$ each independently represent a $C_{1-4}$ alkyl group; p' represents an integer from 0 to 3; and r' represents an integer from 0 to 2.)

The rare earth atom represented by $M^2$ in this rare earth element-containing precursor can be exemplified by scandium, yttrium, lanthanum, cerium, praseodymium, neodymium, promethium, samarium, europium, gadolinium, terbium, dysprosium, holmium, erbium, thulium, ytterbium, and lutetium. The groups represented by $R^a$, $R^b$, $R^c$, $R^e$, $R^f$, $R^g$, and $R^j$ can be exemplified by the groups provided above as examples for the titanium precursors.

The thin film-forming starting material of the present invention may as necessary contain a nucleophilic reagent in order to impart stability to the alkoxide compound of the present invention and the additional precursor. This nucleophilic reagent can be exemplified by ethylene glycol ethers such as glyme, diglyme, triglyme, and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-ketoesters such as methyl acetoacetate, ethyl acetoacetate, and 2-methoxyethyl acetoacetate; and β-diketones such as acetylacetone, 2,4-hexanedione, 2,4-heptanedione, 3,5-heptanedione, and dipivaloylmethane. The amount of nucleophilic reagent used per 1 mol of the total amount of the precursor is preferably in the range from 0.1 mol to 10 mol and more preferably is 1 to 4 mol.

To the greatest extent possible, the thin film-forming starting material of the present invention does not contain, other than its constituent components, metal element impurities, halogen impurities such as chlorine impurities, and organic impurities. The metal element impurities are, per element, preferably not more than 100 ppb and more preferably not more than 10 ppb, while the total amount is preferably not more than 1 ppm and more preferably not more than 100 ppb. In the particular case of use as an LSI gate dielectric film, gate film, or barrier layer, the content of alkali metal elements and alkaline-earth metal elements, which affect the electrical characteristics of the obtained thin film, must be minimized. The amount of halogen impurity is preferably not more than 100 ppm, more preferably not more than 10 ppm, and most preferably not more than 1 ppm. The total amount of organic impurity is preferably not more than 500 ppm, more preferably not more than 50 ppm, and most preferably not more than 10 ppm. Moisture causes the generation of particles in the chemical vapor deposition starting material and the generation of particles during thin film formation and because of this the moisture is desirably preliminarily removed to the greatest extent possible from the metal compound, organic solvent, and nucleophilic reagent at the time of use in order to reduce the moisture in each. The amount of moisture in each of the metal compound, organic solvent, and nucleophilic reagent is preferably not more than 10 ppm and more preferably not more than 1 ppm.

In order to reduce or prevent particle contamination of the thin film that is formed, the thin film-forming starting material of the present invention preferably contains as little particulate as possible. Specifically, in particle measurement in the liquid phase using a light-scattering detector for liquid-borne particles, the number of particles larger than 0.3 µm in 1 mL of the liquid phase is preferably not more than 100; the number of particles larger than 0.2 µm in 1 mL of the liquid phase is more preferably not more than 1,000; and the number of particles larger than 0.2 µm in 1 mL of the liquid phase is most preferably not more than 100.

The thin film production method of the present invention, which produces a thin film by using the thin film-forming starting material of the present invention, proceeds according to a CVD method in which a vapor produced by vaporizing the thin film-forming starting material of the present invention and a reactive gas used on an optional basis are introduced into a film-formation chamber in which a substrate is disposed and a metal-containing thin film is grown and deposited on a substrate surface by the decomposition and/or chemical reaction of the precursor on the substrate. The method for transporting and supplying the starting material, the deposition method, the production conditions, the production apparatus, and so forth are not particularly limited and commonly known conditions and methods can be used.

The aforementioned reactive gas used on an optional basis can be exemplified by oxidizing gases such as oxygen, ozone, nitrogen dioxide, nitric oxide, water vapor, hydrogen peroxide, formic acid, acetic acid, and acetic anhydride; by reducing gases such as hydrogen; and by gases that produce nitride, such as hydrazine, ammonia, and organic amine compounds such as monoalkylamine, dialkylamine, trialkylamine, and alkylenediamine. A single one of these may be used or two or more may be used.

The transport and supply method can be exemplified by the previously described gas transport method, liquid transport method, single-source method, and cocktail-source method.

The deposition method can be exemplified by thermal CVD, in which a thin film is deposited by causing the starting material gas, or the starting material gas and a reactive gas, to react only through the application of heat; plasma CVD, which uses heat and a plasma; photo-CVD, which uses heat and light; plasma photo-CVD, which uses heat, light, and a plasma; and ALD, in which deposition is carried out stepwise at the molecular level by dividing the CVD deposition reactions into elementary processes.

The material of the substrate can be exemplified by silicon; ceramics, e.g., silicon nitride, titanium nitride, tantalumnitride, titanium oxide, titanium nitride, ruthenium oxide, zirconium oxide, hafnium oxide, and lanthanum oxide; glasses; and metals such as ruthenium metal. The shape of the substrate can be exemplified by plate shaped, spherical, fibrous, and scale shaped, and the substrate surface may be flat or may assume a three-dimensional structure, e.g., a trench structure and so forth.

The production conditions referenced above are, for example, the reaction temperature (substrate temperature), reaction pressure, deposition rate, and so forth. With regard to the reaction temperature, 100° C. or above—which are temperatures at which the alkoxide compound of the present invention is thoroughly reacted—is preferred and 150° C. to 400° C. is more preferred. 150° C. to 250° C. is particularly preferred because the alkoxide compound of the present invention can undergo thermal decomposition at below 200° C. In addition, the reaction pressure is preferably atmospheric pressure to 10 Pa in the case of thermal CVD and photo-CVD and is preferably 2,000 Pa to 10 Pa when a plasma is used.

The deposition rate can be controlled using the conditions for starting material supply (vaporization temperature, vaporization pressure), the reaction temperature, and the reaction pressure. Since a high deposition rate can result in a deterioration of the characteristics of the obtained thin film and a low deposition rate can produce productivity issues, the deposition rate is preferably 0.01 to 100 nm/minute and is more preferably 1 to 50 nm/minute. With an ALD method, control is exercised using the number of cycles so as to obtain the desired film thickness.

Other production conditions are the temperature and pressure during production of the vapor by vaporizing the thin film-forming starting material. The step of producing the vapor by vaporization of the thin film-forming starting material can be carried out in the starting material container or in a vaporizer. In either case, the thin film-forming starting material of the present invention is preferably vaporized at 0 to 150° C. In addition, when a vapor is prepared by vaporizing the thin film-forming starting material within the starting material container or a vaporizer, the pressure within the starting material container or the pressure within the vaporizer is preferably 1 to 10,000 Pa in either case.

When the thin film formation method of the present invention uses an ALD method, the following steps may be included in addition to the starting material introduction step in which a vapor is produced by vaporizing the thin film-forming starting material and this vapor is introduced into the film-formation chamber: a precursor thin film formation step, in which a precursor thin film is formed on the surface of the substrate by the alkoxide compound in the vapor; an exhaust step, in which the unreacted alkoxide compound gas is exhausted; and a step of forming a metal-containing thin film, in which a metal-containing thin film is formed on the surface of the substrate by chemical reaction of the precursor thin film with reactive gas.

Each of the steps referenced above is described in detail in the following using the formation of a metal oxide thin film as an example. The starting material introduction step described above is carried out first in the case of formation of a metal oxide thin film using the ALD method. The preferred temperature and pressure for conversion of the thin film-forming starting material to the vapor is the same as already described above. The precursor thin film is then formed on a substrate surface by the alkoxide compound that has been introduced into the deposition reaction section (precursor thin film formation step). During this, the application of heat may be carried out by heating the substrate or by heating the deposition reaction section. The precursor thin film formed in this step is a metal oxide thin film, or is a thin film produced by the decomposition and/or reaction of a portion of the alkoxide compound, and has a composition different from that of the target metal oxide thin film. The substrate temperature during the execution of this step is preferably room temperature to 500° C. and is more preferably 150 to 350° C. The pressure in the system (within the film-formation chamber) during the execution of this step is preferably 1 to 10,000 Pa and more preferably 10 to 1,000 Pa.

The unreacted alkoxide compound gas and by-product gas are then exhausted from the deposition reaction section (exhaust step). Complete exhaust of the unreacted alkoxide compound gas and by-product gas from the deposition reaction section is the ideal, but complete exhaust is not necessarily required. The exhaust method can be exemplified by the following: methods in which the interior of the system is purged using an inert gas such as nitrogen, helium, or argon; methods in which exhaust is performed by reducing the pressure in the system; and methods that combine the preceding. In the case of pressure reduction, the vacuum is preferably 0.01 to 300 Pa and is more preferably 0.01 to 100 Pa.

Then, an oxidizing gas is introduced into the deposition reaction section and a metal oxide thin film is formed through the action of the oxidizing gas or through the action of the oxidizing gas and heat from the precursor thin film obtained in the preceding precursor thin film formation step (metal oxide-containing thin film formation step). The temperature in this step when the action of heat is employed is preferably room temperature to 500° C. and more preferably 150 to 350° C. The pressure in the system (within the film-formation chamber) during the execution of this step is preferably 1 to 10,000 Pa and more preferably 10 to 1,000 Pa. The alkoxide compound of the present invention has an excellent reactivity with oxidizing gases and can produce metal oxide thin films.

When the ALD method as described above is used in the thin film formation method of the present invention, and taking 1 cycle to be thin film deposition by a process chain composed of the previously described starting material introduction step, precursor thin film formation step, exhaust step, and metal oxide-containing thin film formation step, this cycle is repeated a plurality of times until a thin film of the required film thickness is obtained. In this case, after 1 cycle has been executed, the ensuing cycle is preferably carried out after exhausting from the deposition reaction section, proceeding in the same manner as for the exhaust step, the unreacted alkoxide compound gas and reactive gas (an oxidizing gas when a metal oxide thin film is being formed) and also the by-product gas.

In addition, energy, e.g., plasma, light, voltage, and so forth, may be applied and a catalyst may be used in the formation of a metal oxide thin film by the ALD method. The timing of the application of energy and the timing for catalyst use are not particularly limited and, for example, may be during the introduction of the alkoxide compound gas in the starting material introduction step, during the heating in the precursor thin film formation step or the metal oxide-containing thin film formation step, during exhaust of the system interior in the exhaust step, during the introduction of the oxidizing gas in the metal oxide-containing thin film formation step, and between these steps.

In order to obtain even better electrical characteristics, thin film deposition in the thin film formation method of the present invention may be followed by the execution of an annealing process under an inert atmosphere, an oxidizing atmosphere, or a reducing atmosphere, while a reflow step may also be implemented when step coverage is required. The temperature in this case is 200 to 1,000° C. and preferably 250 to 500° C.

A known chemical vapor deposition apparatus can be used as the apparatus for producing a thin film using the thin film-forming starting material of the present invention. Specific examples of the apparatus are the apparatus shown in FIG. 1, which operates through the bubbling supply of the precursor, and the apparatus shown in FIG. 2, which has a vaporizer. Other examples are the apparatuses shown in FIGS. 3 and 4, which can carry out a plasma treatment on the reactive gas. There is no limitation to the single-wafer apparatuses shown in FIGS. 1 to 4, and an apparatus capable of the simultaneous processing of a plurality of wafers using a batch furnace can also be used.

The thin film produced using the thin film-forming starting material of the present invention can be produced in the desired species of thin film, e.g., metal, oxide ceramic, nitride ceramic, glass, and so forth, by the appropriate selection of the additional precursor, the reactive gas, and the production conditions. These thin films are known to exhibit, inter alia, various electrical properties and optical properties and are used in a variety of applications. For example, copper and copper-containing thin films exhibit the properties of a high electrical conductivity, a high resistance to electromigration, and a high melting point and as a result are used as LSI interconnect materials. In addition, nickel and nickel-containing thin films are used mainly, for example, for electronic component members, e.g., resistive films and barrier films, for recording media members, e.g., magnetic films, and for members for thin-film solar cells, e.g., electrodes. Cobalt and cobalt-containing thin films are used, for example, for electrode films, resistive films, adhesive films, magnetic tapes, and carbide tool members.

The alcohol compound of the present invention is represented by the following general formula (II) and is a compound that is particularly well suited as a ligand for use in compounds that are advantageous as precursors in thin film formation methods that have a vaporization step, e.g., CVD methods and so forth.

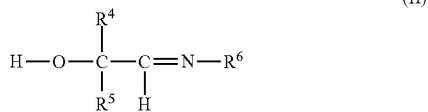

(II)

(In the formula, $R^4$ and $R^5$ each independently represent a hydrogen atom, a $C_{1-12}$ hydrocarbon group, or a group represented by any of the following general formulas (Y-1) to (Y-8). $R^6$ represents a hydrogen atom or a $C_{1-3}$ hydrocarbon group or a group represented by any of the following general formulas (Y-1) to (Y-8). However, when $R^4$ is a methyl group and $R^5$ is a methyl group or an ethyl group, $R^6$ represents a hydrogen atom or a group represented by any of the following general formulas (Y-1) to (Y-8).)

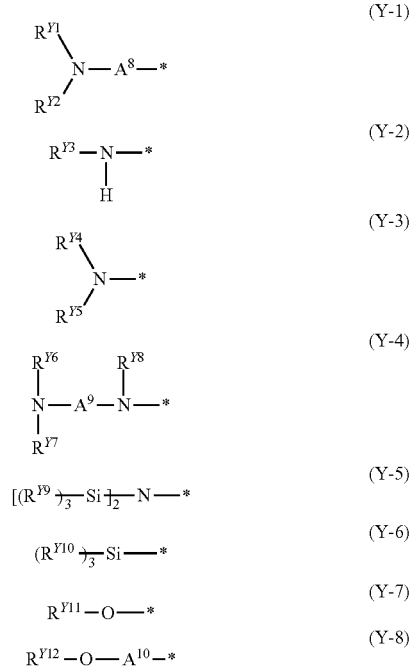

(Y-1)

(Y-2)

(Y-3)

(Y-4)

(Y-5)

(Y-6)

(Y-7)

(Y-8)

(In the formulas, $R^{Y1}$ to $R^{Y12}$ each independently represent a hydrogen atom or a $C_{1-12}$ hydrocarbon group, and $A^8$ to $A^{10}$ represent a $C_{1-6}$ alkanediyl group.)

$R^4$ and $R^5$ in general formula (II) each independently represent a hydrogen atom, a $C_{1-12}$ hydrocarbon group, or a group represented by any of general formulas (Y-1) to (Y-8).

For example, alkyl, alkenyl, cycloalkyl, aryl, and cyclopentadienyl can be used for the hydrocarbon groups represented by $R^4$ and $R^5$.

The alkyl can be exemplified by methyl, ethyl, propyl, isopropyl, butyl, isobutyl, sec-butyl, tert-butyl, pentyl, amyl, isoamyl, hexyl, heptyl, isoheptyl, octyl, isooctyl, 2-ethylhexyl, nonyl, isononyl, decyl, and dodecyl.

The alkenyl can be exemplified by vinyl, 1-methylethenyl, 2-methylethenyl, propenyl, butenyl, isobutenyl, pentenyl, hexenyl, heptenyl, octenyl, and decenyl.

The cycloalkyl can be exemplified by cyclohexyl, cyclopentyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

The aryl can be exemplified by phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tertiary-butylphenyl, 4-hexylphenyl, and 4-cyclohexylphenyl.

The cyclopentadienyl can be exemplified by cyclopentadienyl, methylcyclopentadienyl, ethylcyclopentadienyl, propylcyclopentadienyl, isopropylcyclopentadienyl, butylcyclopentadienyl, sec-butylcyclopentadienyl, isobutylcyclopentadienyl, tert-butylcyclopentadienyl, dimethylcyclopentadienyl, and tetramethylcyclopentadienyl.

$R^6$ in general formula (II) represents a hydrogen atom or a $C_{1-3}$ hydrocarbon group or a group represented by any of general formulas (Y-1) to (Y-8).

Specific examples of the hydrocarbon groups represented by $R^6$ are methyl, ethyl, propyl, isopropyl, vinyl, 1-methylethenyl, 2-methylethenyl, and propenyl.

When $R^4$ in general formula (II) is a methyl group and $R^5$ is a methyl group or an ethyl group, $R^6$ represents a hydrogen atom or a group represented by any of general formulas (Y-1) to (Y-8).

The $C_{1-12}$ hydrocarbon groups represented by $R^{Y1}$ to $R^{Y12}$ can be specifically exemplified by the same groups as the groups provided as examples of the $C_{1-12}$ hydrocarbon groups represented by $R^4$ and $R^5$.

The $C_{1-6}$ alkanediyl groups represented by $A^8$ to $A^{10}$ can be exemplified by methylene, ethylene, propylene, and butylene.

The group represented by general formula (Y-1) can be exemplified by dimethylaminomethyl, ethylmethylaminomethyl, diethylaminomethyl, dimethylaminoethyl, ethylmethylaminoethyl, and diethylaminoethyl.

The group represented by general formula (Y-2) can be exemplified by methylamino, ethylamino, propylamino, isopropylamino, butylamino, sec-butylamino, tert-butylamino, and isobutylamino.

The group represented by general formula (Y-3) can be exemplified by dimethylamino, diethylamino, dipropylamino, diisopropylamino, dibutylamino, di-sec-butylamino, di-tert-butylamino, ethylmethylamino, propylmethylamino, and isopropylmethylamino.

Compounds that contribute the group represented by general formula (Y-4) can be exemplified by ethylenediamino, hexamethylenediamino, and N,N-dimethylethylenediamino.

The group represented by general formula (Y-5) can be exemplified by di(trimethylsilyl)amino and di(triethylsilyl)amino.

The group represented by general formula (Y-6) can be exemplified by trimethylsilyl and triethylsilyl.

The group represented by general formula (Y-7) can be exemplified by methoxy, ethoxy, propoxy, isopropoxy, butoxy, sec-butoxy, isobutoxy, tert-butoxy, pentoxy, isopentoxy, and tert-pentoxy.

The group represented by general formula (Y-8) can be exemplified by hydroxymethyl, hydroxyethyl, hydroxypropyl, hydroxyisopropyl, and hydroxybutyl.

Optical isomers may also exist for the alcohol compound of the present invention, but the alcohol compound of the present invention is not distinguished with regard to its optical isomerism.

Preferred specific examples of the alcohol compound represented by general formula (II) are, for example, the compounds represented by the following chemical formulas No. 92 to No. 170. In the following chemical formulas, "Me" represents methyl; "Et" represents ethyl; and "iPr" represents isopropyl.
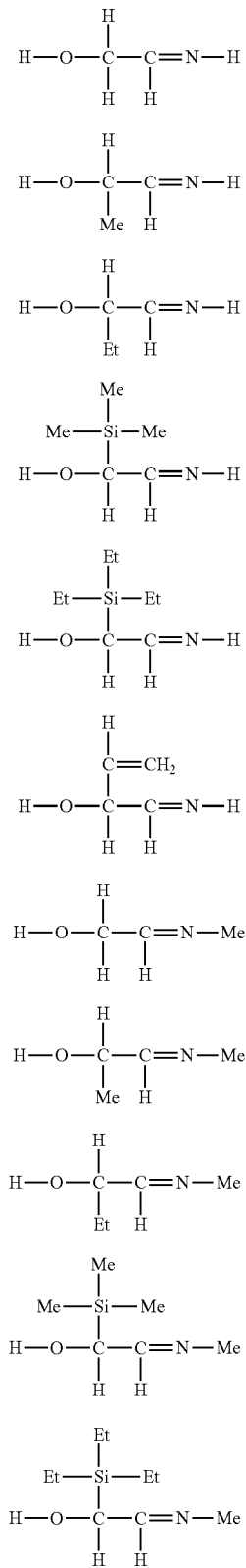
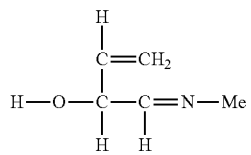
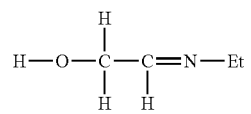
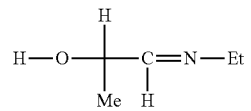
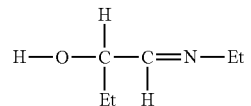
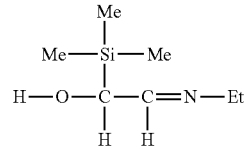
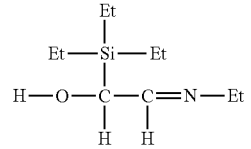
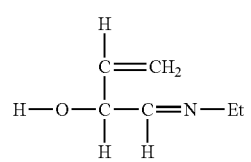
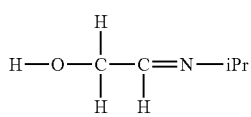
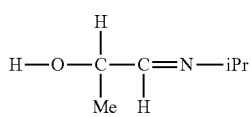
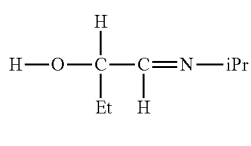
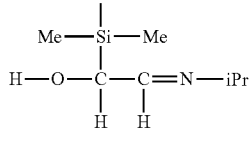

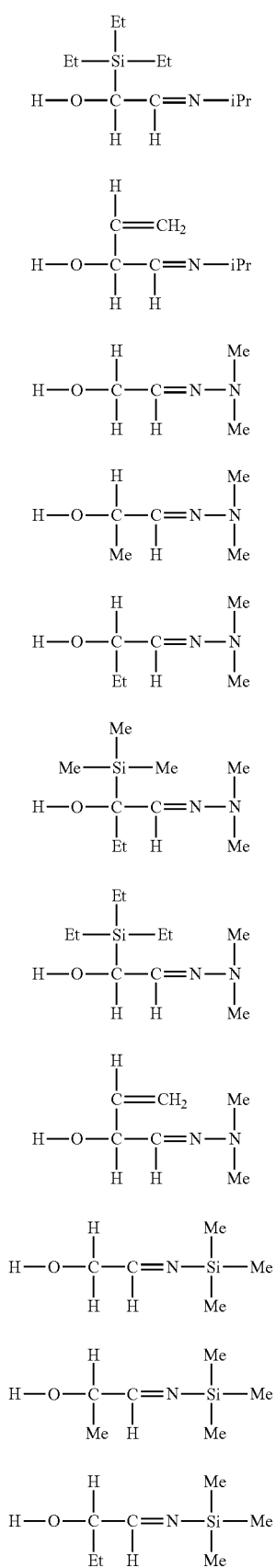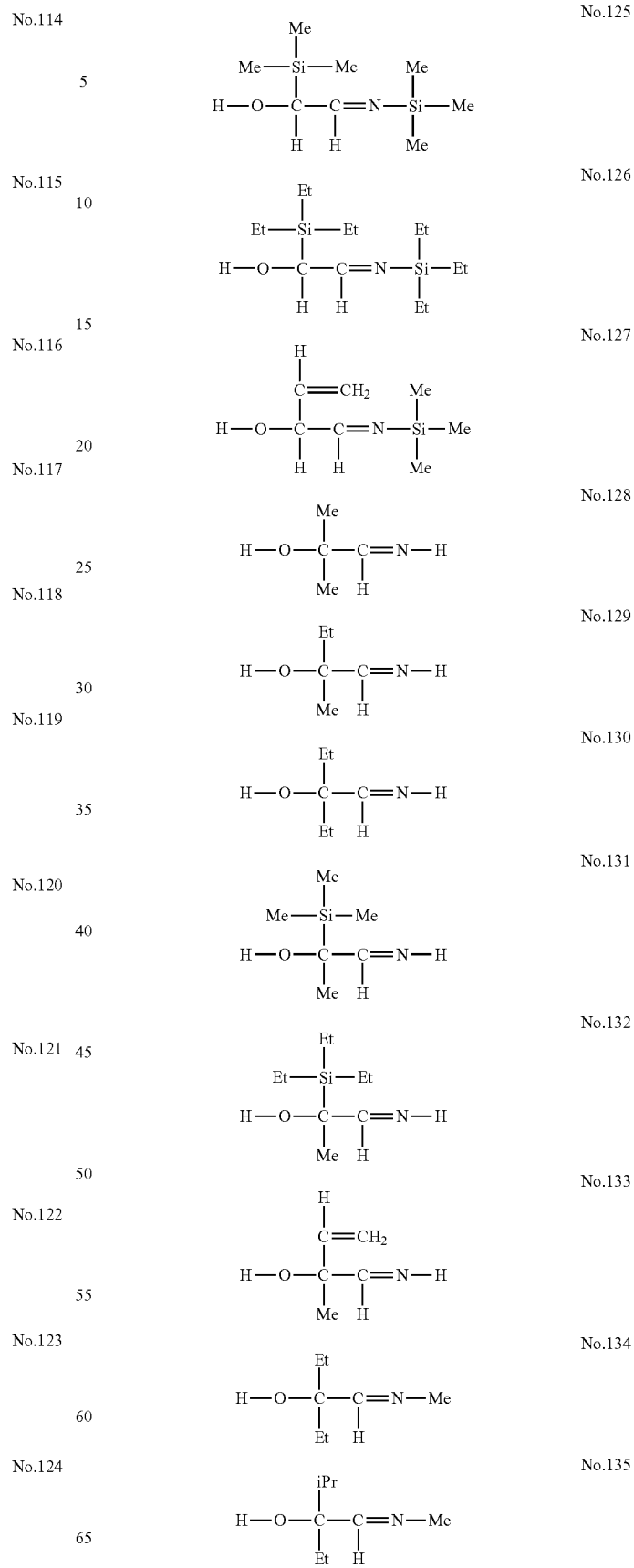

-continued
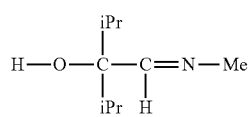
No.136
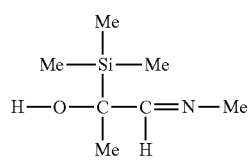
No.137
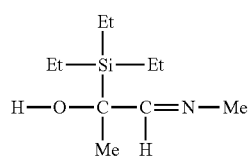
No.138
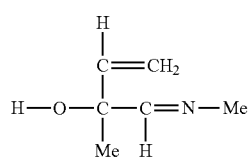
No.139
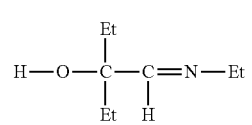
No.140
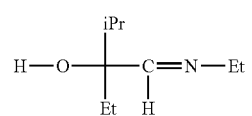
No.141
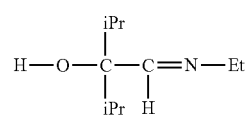
No.142
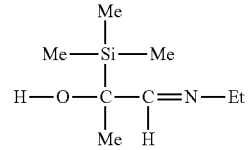
No.143
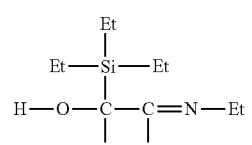
No.144
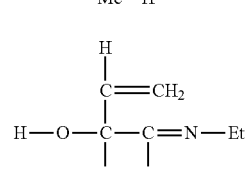
No.145
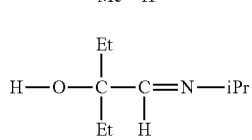
No.146
-continued
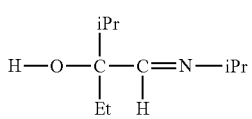
No.147
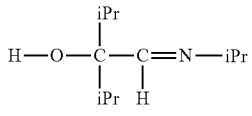
No.148
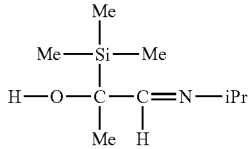
No.149
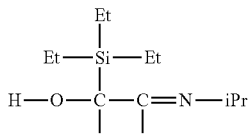
No.150
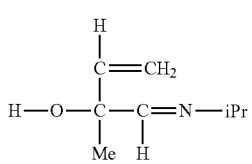
No.151
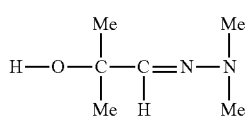
No.152
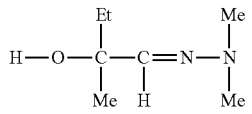
No.153
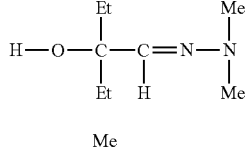
No.154
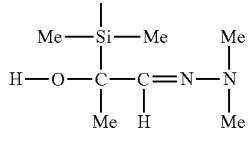
No.155
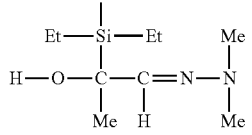
No.156
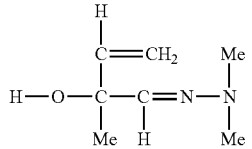
No.157

-continued

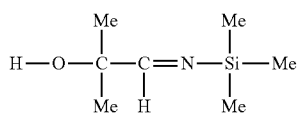
No.158

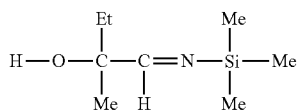
No.159

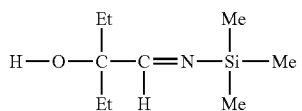
No.160

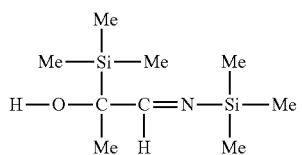
No.161

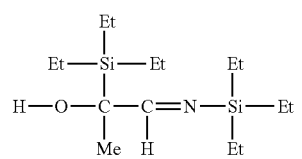
No.162

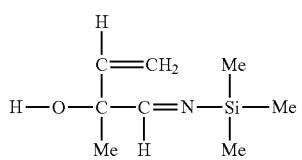
No.163

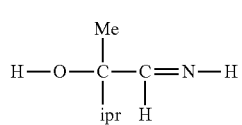
No.164

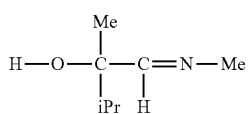
No.165

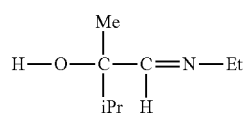
No.166

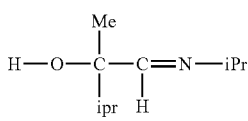
No.167

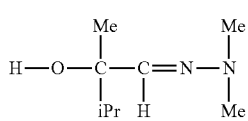
No.168

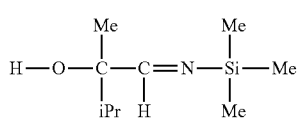
No.169

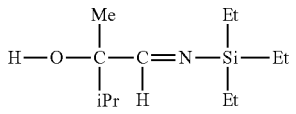
No.170

The alcohol compound of the present invention is not particularly limited with regard to its method of production, and it can be produced by the application of known reactions.

The following are examples: a method as shown in the following reaction formula (1), in which a Grignard reaction is run between an alkyl compound and an alkyl alkoxycarboxylate compound using magnesium as a catalyst, and an additional reaction with an alkylamine is carried out followed by extraction of the reaction product with a suitable solvent and a drying treatment; a method as shown in the following reaction formula (2), in which a Grignard reaction is run between an alkyl compound and an alkoxy ketone alkyl compound using magnesium as a catalyst, and an additional reaction with an alkylamine is carried out followed by extraction of the reaction product with a suitable solvent and a drying treatment; and a method as shown in the following reaction formula (3), in which a Grignard reaction is run between an alkyl compound and a dialkyl diketone compound using magnesium as a catalyst, and an additional reaction with an alkylamine is carried out followed by extraction with a suitable solvent and a drying treatment.

Reaction Formula (1)
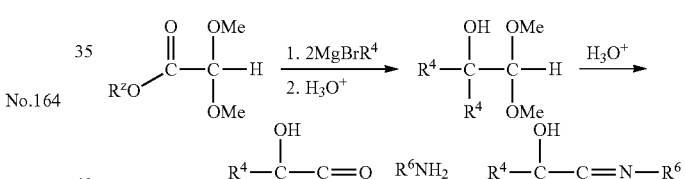

Reaction Formula (2)
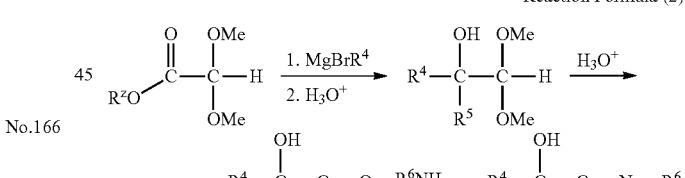

Reaction Formula (3)
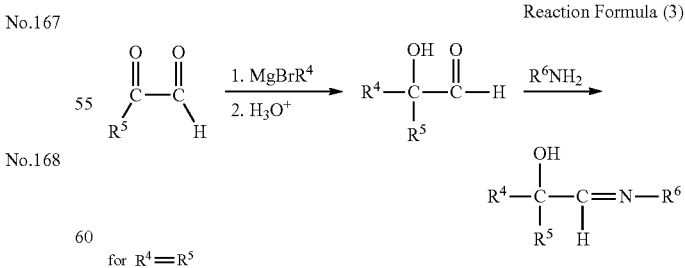

[$R^z$ in reaction formula (1) and reaction formula (2) represents an alkyl group.]

The alcohol compound of the present invention can be used as a ligand in a metal compound used for, inter alia, a thin film-forming starting material. In addition, the alcohol compound of the present invention can also be used, for example, as a synthesis starting material for solvents, fragrances, agrochemicals, pharmaceuticals, various polymers, and so forth.

EXAMPLES

The present invention is described in additional detail below using examples and evaluation examples. However, the present invention is in no way limited to or by the following examples.

Example 1: Synthesis of Alcohol Compound No. 134

22.43 g of 3-dimethoxymethyl-3-pentanol, 40 g of pure water, and 3.6 g of 36% hydrochloric acid were added under ice cooling to a reaction flask and stirring was carried out for 5 hours. This was followed by the dropwise addition of 23.72 g of a 40% aqueous methylamine solution with ice cooling and reaction for 17 hours. The pH of the reaction solution at this time was 10 to 11. 32.9 g of toluene was added; the organic layer was extracted and separated; and magnesium sulfate was added and drying and filtration were performed. The solvent was distilled off on an oil bath at 90° C. under reduced pressure to obtain alcohol compound No. 134. 7.69 g was obtained for a yield of 43%.

(Analytic Values)
(1) GC-MS m/z: 129 (M+)
(3) elementary analysis: C: 65.4 mass %, H: 12.1 mass %, O: 11.2 mass %, N: 11.3 mass % (theoretical values: C: 65.1 mass %, H: 11.7 mass %, O: 12.4 mass %, N: 10.8 mass %)

Example 2: Synthesis of Alcohol Compound No. 140

A diethyl ether solution of ethylmagnesium bromide (concentration=21.85 mass %, 277 g) was added to a reaction flask and was cooled to around 0° C. by stirring on an ice-cooling bath. A Grignard reaction was carried out by the dropwise addition to this solution over one hour of methyl dimethoxyacetate (25 g). This was followed by return to room temperature and reaction for 12 hours. The reaction solution was ice-cooled; 200 g of a saturated aqueous ammonium chloride solution was added dropwise; and the pH was subsequently adjusted to around neutrality by the dropwise addition of 10 mL of a 36% hydrochloric acid solution. The solution was then transferred to a separatory funnel; the organics were extracted with 50 g of hexane and separated; and drying was carried out over an appropriate amount of magnesium sulfate. This hexane suspension was filtered followed by removal of the solvent on an oil bath at around 65° C. Distillation was performed under reduced pressure on an oil bath at around 100° C. to obtain 22.4 g of a transparent and colorless 3-dimethoxymethyl-3-pentanol (GC purity=96.3%). 10 g of pure water and 1 g of 36% hydrochloric acid were added under ice cooling to 7 g of the 3-dimethoxymethyl-3-pentanol and stirring was carried out overnight. After this, 9.5 g of a 33% aqueous ethylamine solution was added dropwise under ice cooling and a reaction was run for 10 hours. The pH of the reaction solution at this time was 10 to 11. When stirring was stopped, separation occurred into an aqueous layer and a small amount of an organic layer, and the organic layer was determined to be alcohol compound No. 140 according to the NMR results. 2.7 g of the target was obtained for a yield of 33%.

(Analytic Values)
(1) GC-MS m/z: 143 (M+)
(2) $^1$NMR (solvent: deuterobenzene) (chemical shift: multiplicity: number of H)
(7.020: s: 1) (4.379: s: 1) (3.171-3.193: q: 2) (1.559-1.649 m: 2) (1.310-1.400: m: 2) (0.979-1.016: t: 3) (0.837-0.874: t: 6)
(3) elementary analysis: C: 67.5 mass %, H: 12.1 mass %, O: 12.0 mass %, N: 9.6 mass % (theoretical values: C: 67.1 mass %, H: 12.0 mass %, O: 11.2 mass %, N: 9.8 mass %)

Example 3: Synthesis of Alcohol Compound No. 146

19.67 g of 3-dimethoxymethyl-3-pentanol, 35 g of pure water, and 8.9 g of 36% hydrochloric acid were added under ice cooling to a reaction flask and stirring was performed for 4 hours. 16.67 g of isopropylamine was then added dropwise under ice cooling and a reaction was carried out for 18 hours. The pH of the reaction solution at this time was 10 to 11. 28.8 g of toluene was added; the organic layer was extracted and separated; and magnesium sulfate was added and drying and filtration were carried out. The solvent was distilled off on an oil bath at 90° C. under reduced pressure to obtain alcohol compound No. 146. 13.48 g was obtained for a yield of 69%.

(Analytic Values)
(1) GC-MS m/z: 157 (M+)
(3) elementary analysis: C: 69.0 mass %, H: 11.9 mass %, O: 11.0 mass %, N: 8.9 mass % (theoretical values: C: 68.7 mass %, H: 12.2 mass %, O: 10.2 mass %, N: 8.9 mass %)

Example 4: Synthesis of Alcohol Compound No. 166

2.17 g of magnesium and 118 g of tetrahydrofuran were introduced into a reaction flask and 11.3 g of 2-bromopropane was gradually added dropwise to this at a bath temperature of 50° C. After cooling to room temperature and stirring for 2 hours, 10.3 g of pyruvic aldehyde dimethyl acetal was gradually added dropwise and stirring was performed for 20 hours at room temperature. Quenching was performed by the addition of 39 g of an 8% aqueous hydrochloric acid solution and 25.3 g of ammonium chloride. To this was added 26.7 g of hexane and the target material (intermediate) was extracted into the organic layer and was dried over sodium sulfate followed by filtration. The hexane was distilled off at a bath temperature of 85° C. under a slight pressure reduction and the obtained residue was distilled under a slight pressure reduction at a column top temperature of 50° C. and a bath temperature of 85° C. to obtain the intermediate 1,1-dimethoxy-2,3-dimethyl-2-butanol. 18.5 g of H$_2$O was added to 6.0 g of the 1,1-dimethoxy-2,3-dimethyl-2-butanol and to this was gradually added dropwise at room temperature 2.1 g of a 36% aqueous hydrochloric acid solution. After stirring for 2 hours, 15.3 g of a 33% aqueous ethylamine solution was gradually added dropwise under water cooling. After stirring for 20 hours at room temperature, 31.2 g of toluene was added and the target material was extracted into the organic layer. Drying over sodium sulfate was carried out followed by filtration, and the toluene was distilled off at a bath temperature of 85° C. under a slightly reduced pressure. The obtained residue was distilled under a slightly reduced pressure at a bath temperature of 85° C. to obtain alcohol compound No. 166. 3.6 g (GC purity=92%) was obtained for a yield of 27%.

(Analytic Values)
(1) GC-MS m/z: 143 (M+)
(3) elementary analysis: C: 67.4 mass %, H: 12.3 mass %, O: 10.5 mass %, N: 9.4 mass % (theoretical values: C: 67.0 mass %, H: 12.0 mass %, O: 11.2 mass %, N: 9.8 mass %)

Example 5: Synthesis of Alcohol Compound No. 167

10.0 g of 1,1-dimethoxy-2,3-dimethyl-2-butanol (90% pure product) and 10.0 g of $H_2O$ were introduced into a reaction flask; to this was gradually added dropwise 1.5 g of a 36% aqueous hydrochloric acid solution with ice cooling; and stirring was performed for 20 hours at room temperature. 11.5 g of isopropylamine was gradually added dropwise with ice cooling and, after warming to room temperature, stirring was performed for 20 hours. 70 g of toluene was added and the target material was extracted into the organic layer. Drying over sodium sulfate and filtration were carried out. A toluene solution (3.19 mass %) of 1-isopropylimino-2,3-dimethyl-2-butanol was obtained. The solvent was distilled off on an oil bath at 90° C. under reduced pressure to obtain alcohol compound No. 167.
(Analytic Values)
(1) GC-MS m/z: 157 (M+)
(3) elementary analysis: C: 69.0 mass %, H: 11.9 mass %, O: 10.6 mass %, N: 8.8 mass % (theoretical values: C: 68.7 mass %, H: 12.2 mass %, O: 10.2 mass %, N: 8.9 mass %)

Example 6: Synthesis of Alkoxide Compound No. 43

4.04 g of cobalt(II) chloride and 16 g of tetrahydrofuran were introduced into a 200-mL four-neck flask and were stirred at room temperature. To this was added dropwise with ice cooling a solution prepared by the dilution, with 17 g of tetrahydrofuran, of 8.77 g of the sodium alkoxide prepared from alcohol compound No. 134 (3-methyliminomethyl-3-pentanol). After the completion of the dropwise addition, stirring was performed for 16 hours at room temperature followed by filtration. The tetrahydrofuran was removed from the obtained filtrate and the residue was distilled under conditions of 60 Pa and 130° C. to obtain 1.34 g of alkoxide compound No. 43 for a yield of 14.5%.
(Analytic Values)
(1) Vacuum TG-DTA
50% mass loss temperature: 136.2° C. (10 Torr, Ar flow rate: 50 mL/minute, heating at 10° C./minute)
(2) elementary analysis: Co: 18.4 mass %, C: 53.6 mass %, H: 8.7 mass %, O: 10.6 mass %, N: 8.6 mass % (theoretical values: Co: 18.7 mass %, C: 53.3 mass %, H: 9.0 mass %, O: 10.1 mass %, N: 8.9 mass %)

Example 7: Synthesis of Alkoxide Compound No. 49

Figure 5:
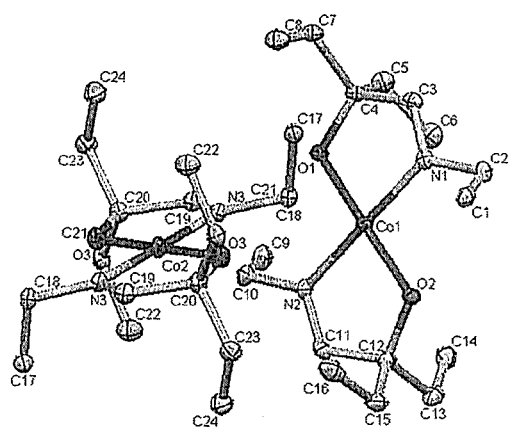
FIG. 5 is a molecular structure diagram, obtained by single-crystal X-ray structural analysis, of alkoxide compound No. 49.

13.23 g of cobalt(II) chloride and 48 g of tetrahydrofuran were introduced into a 200-mL four-neck flask and were stirred at room temperature. To this was added dropwise with ice cooling a solution prepared by the dilution, with 50 g of tetrahydrofuran, of 33.04 g of the sodium alkoxide prepared from alcohol compound No. 140 (3-ethyliminomethyl-3-pentanol). After the completion of the dropwise addition, stirring was performed for 22 hours at room temperature followed by filtration. The tetrahydrofuran was removed from the obtained filtrate and the residue was distilled under conditions of 40 Pa and 125° C. to obtain 28.70 g of alkoxide compound No. 49 for a yield of 83.5%. The results of single-crystal X-ray structural analysis of the obtained alkoxide compound No. 49 are shown in FIG. 5.
(Analytic Values)
(1) Vacuum TG-DTA
50% mass loss temperature: 125.8° C. (10 Torr, Ar flow rate: 50 mL/minute, heating at 10° C./minute)
(2) elementary analysis: Co: 16.5 mass %, C: 56.3 mass %, H: 9.5 mass %, O: 9.8 mass %, N: 7.9 mass % (theoretical values: Co: 17.2 mass %, C: 56.0 mass %, H: 9.4 mass %, O: 9.3 mass %, N: 8.2 mass %)

Example 8: Synthesis of Alkoxide Compound No. 55

5.75 g of cobalt(II) chloride and 18 g of tetrahydrofuran were introduced into a 200-mL four-neck flask and were stirred at room temperature. To this was added dropwise with ice cooling a solution prepared by the dilution, with 17 g of tetrahydrofuran, of 15.06 g of the sodium alkoxide prepared from alcohol compound No. 146 (3-isopropyliminomethyl-3-pentanol). After the completion of the dropwise addition, stirring was performed for 29 hours at room temperature followed by filtration. The tetrahydrofuran was removed from the obtained filtrate and the residue was distilled under conditions of 50 Pa and 135° C. to obtain 5.53 g of alkoxide compound No. 55 for a yield of 35.1%.
(Analytic Values)
(1) Vacuum TG-DTA
50% mass loss temperature: 130.3° C. (10 Torr, Ar flow rate: 50 mL/minute, heating at 10° C./minute)
(2) elementary analysis: Co: 15.0 mass %, C: 59.0 mass %, H: 9.7 mass %, O: 8.9 mass %, N: 7.5 mass % (theoretical values: Co: 15.9 mass %, C: 58.2 mass %, H: 9.8 mass %, O: 8.6 mass %, N: 7.5 mass %)

Example 9: Synthesis of Alkoxide Compound No. 75

1.52 g of cobalt(II) chloride and 8.22 g of tetrahydrofuran were introduced into a 100-mL three-neck flask and were stirred at room temperature. To this was added dropwise with ice cooling a solution prepared by the dilution, with 7.95 g of tetrahydrofuran, of 3.80 g of the sodium alkoxide prepared from alcohol compound No. 166 (1-ethylimino-2,3-dimethyl-2-butanol). After the completion of the dropwise addition, stirring was performed for 15 hours at room temperature followed by filtration. The tetrahydrofuran was removed from the obtained filtrate and the residue was distilled under conditions of 45 Pa, a bath temperature of 130° C., and a column top temperature of 90° C. to obtain 1.56 g of alkoxide compound No. 75 for a yield of 39.3%.
(Analytic Values)
(1) Vacuum TG-DTA
50% mass loss temperature: 123° C. (10 Torr, Ar flow rate: 50 mL/minute, heating at 10° C./minute)
(2) elementary analysis: Co: 16.9 mass %, C: 56.2 mass %, H: 9.2 mass %, O: 9.7 mass %, N: 8.3 mass % (theoretical values: Co: 17.2 mass %, C: 56.0 mass %, H: 9.4 mass %, O: 9.3 mass %, N: 8.2 mass %)

Example 10: Synthesis of Alkoxide Compound No. 171

Figure 6:
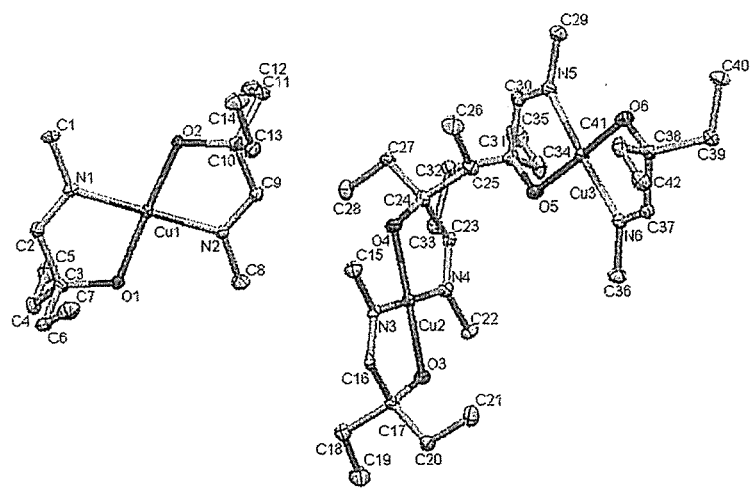
FIG. 6 is a molecular structure diagram, obtained by single-crystal X-ray structural analysis, of alkoxide compound No. 171.

32 g of a 3.8 mass % toluene solution of alcohol compound No. 134 (3-methyliminomethyl-3-pentanol) was added dropwise to 0.59 g of copper(II) methoxide under an argon gas atmosphere. Dissolution occurred rapidly with the assumption of a purple color, and stirring was carried out in this condition for 20 hours at room temperature. The toluene was distilled off under a slightly reduced pressure at an oil bath temperature of 70° C. and the residual toluene was then completely distilled off under reduced pressure at an oil bath temperature of 90° C. The obtained purple solid was distilled at 100° C. and 40 Pa to obtain the target. The obtained compound was a solid with a melting point of 60° C. The yield of this compound was 70%. Single-crystal X-ray structural analysis was performed on the obtained compound. The molecular structure provided by single-crystal X-ray structural analysis is shown in FIG. 6. It could be confirmed from this result that the obtained compound was alkoxide compound No. 171.

(Analytic Values)
(1) Vacuum TG-DTA
50% mass loss temperature: 120° C. (10 Torr, Ar flow rate: 50 mL/minute, heating at 10° C./minute)
(2) elementary analysis: Cu: 19.7 mass %, C: 52.4 mass %, H: 8.9 mass %, O: 10.7 mass %, N: 8.4 mass % (theoretical values: Cu: 19.9 mass %, C: 52.6 mass %, H: 8.8 mass %, O: 10.0 mass %, N: 8.8 mass %)

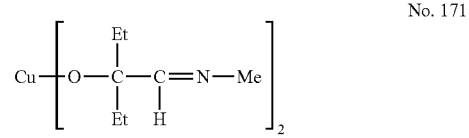

No. 171

Example 11: Synthesis of Alkoxide Compound No. 172

38 g of a 3.7 mass % toluene solution of alcohol compound No. 140 (3-ethyliminomethyl-3-pentanol) was added dropwise to 0.62 g of copper(II) methoxide under an argon gas atmosphere. Dissolution occurred rapidly with the assumption of a purple color, and stirring was carried out in this condition for 18 hours at room temperature. The toluene was distilled off under a slightly reduced pressure at an oil bath temperature of 70° C. and the residual toluene was then completely distilled off under reduced pressure at an oil bath temperature of 90° C. The obtained purple liquid was distilled at 100° C. and 40 Pa to obtain alkoxide compound No. 172 in the form of a purple liquid. The yield of alkoxide compound No. 172 was 45%.

(Analytic Values)
(1) Vacuum TG-DTA
50% mass loss temperature: 120° C. (10 Torr, Ar flow rate: 50 mL/minute, heating at 10° C./minute)
(2) elementary analysis: Cu: 18.4 mass %, C: 54.9 mass %, H: 8.8 mass %, O: 9.0 mass %, N: 8.2 mass % (theoretical values: Cu: 18.3 mass %, C: 55.2 mass %, H: 9.3 mass %, O: 9.2 mass %, N: 8.1 mass %)

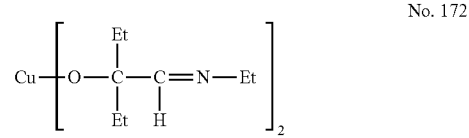

No. 172

Example 12: Synthesis of Alkoxide Compound No. 221

4.97 g of hexaamminenickel(II) chloride and 95 g of tetrahydrofuran were introduced into a 500-mL four-neck flask and were stirred at room temperature. To this was added dropwise with ice cooling a solution prepared by the dilution, with 180 g of tetrahydrofuran, of the sodium alkoxide prepared from 36.0 g of a 17.2 mass % toluene solution of the alcohol (3-ethyliminomethyl-3-pentanol). After the completion of the dropwise addition, stirring was carried out with heating to 70° C., followed by removal of the tetrahydrofuran and toluene. The residue was dissolved in hexane and filtration was performed. The hexane was removed from the obtained filtrate and the residue was purified under conditions of 25 Pa and 100° C. to obtain 2.80 g of compound No. 221 for a yield of 37.8%.

(Analytic Values)
(1) Vacuum TG-DTA
50% mass loss temperature: 134° C. (10 Torr, Ar flow rate: 50 mL/minute, heating at 10° C./minute)
(2) elementary analysis: Ni: 17.3 mass %, C: 56.2 mass %, H: 9.2 mass %, O: 9.2 mass %, N: 8.0 mass % (theoretical values: Ni: 17.10 mass %, C: 56.01 mass %, H: 9.40 mass %, O: 9.33 mass %, N: 8.16 mass %)
(3) $^1$NMR (solvent: deuterobenzene) (chemical shift: multiplicity number of H)
(6.877: s: 2) (2.745-2.797: q: 4) (1.328-1.386: m: 8) (1.229-1.266: t: 12) (1.147-1.182: t: 6)

Example 13: Synthesis of Compound No. 247

6.88 g of hexaamminenickel(II) chloride and 42.8 g of tetrahydrofuran were introduced into a 200-mL four-neck flask and were stirred at room temperature. To this was added dropwise with ice cooling a solution prepared by the dilution, with 42.8 g of tetrahydrofuran, of 9.80 g of the sodium alkoxide prepared from the alcohol (1-ethylimino-2,3-dimethyl-2-butanol). After the completion of the dropwise addition, stirring was carried out for 14 hours at room temperature. Heating was carried out under reflux for 2 hours and, after allowing to cool to room temperature, the tetrahydrofuran was removed under reduced pressure. 65 g of hexane was added to the resulting residue and filtration was performed. The hexane was removed from the obtained filtrate and the residue was distilled under conditions of 50 Pa and 100° C. to obtain 2.50 g of compound No. 247 for a yield of 30.7%.

(Analytic Values)
(1) Vacuum TG-DTA
50% mass loss temperature: 132.9° C. (10 Torr, Ar flow rate: 50 mL/minute, heating at 10° C./minute)
(2) $^1$NMR (solvent: deuterobenzene) (chemical shift: multiplicity number of H)
(7.030: d: 2) (2.932-2.593: m: 4) (1.605-1.509: m: 2) (1.661: dd: 12) (1.084-1.117: m: 12)
(3) elementary analysis: Ni: 17.2 mass %, C: 56.3 mass %, H: 9.0 mass %, O: 9.3 mass %, N: 7.9 mass % (theoretical values: Ni: 17.1 mass %, C: 56.0 mass %, H: 9.40 mass %, O: 9.33 mass %, N: 8.16 mass %)

[Evaluation of Autoignition Behavior]
The presence/absence of autoignition of alkoxide compounds Nos. 43, 49, 55, 75, 171, 172, 221, and 247 was checked by allowing to stand in the atmosphere. The results are shown in Table 1.

TABLE 1

| evaluation example | compound | presence/absence of autoignition |
|---|---|---|
| Evaluation Example 1-1 | compound No. 43 | Absent |
| Evaluation Example 1-2 | compound No. 49 | Absent |
| Evaluation Example 1-3 | compound No. 55 | Absent |
| Evaluation Example 1-4 | compound No. 75 | Absent |
| Evaluation Example 1-5 | compound No. 171 | Absent |
| Evaluation Example 1-6 | compound No. 172 | Absent |
| Evaluation Example 1-7 | compound No. 221 | Absent |
| Evaluation Example 1-8 | compound No. 247 | Absent |

[Evaluation of Thermal Stability]

The initial thermal decomposition temperature was measured using a DSC measurement instrument for alkoxide compounds Nos. 43, 49, 55, 75, 171, 172, 221, and 247 and the comparative compounds 1 to 6 shown below. The results are shown in Table 2.

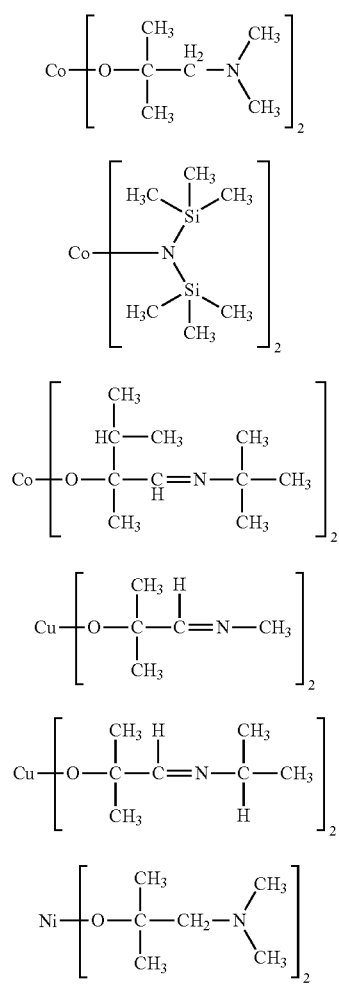

Comparative Compound 1

Comparative Compound 2

Comparative Compound 3

Comparative Compound 4

Comparative Compound 5

Comparative Compound 6

TABLE 2

| evaluation example | compound | initial thermal decomposition temperature |
|---|---|---|
| Evaluation Example 2-1 | compound No. 43 | 190° C. |
| Evaluation Example 2-2 | compound No. 49 | 170° C. |
| Evaluation Example 2-3 | compound No. 55 | 190° C. |

TABLE 2-continued

| evaluation example | compound | initial thermal decomposition temperature |
|---|---|---|
| Evaluation Example 2-4 | compound No. 75 | 170° C. |
| Evaluation Example 2-5 | compound No. 171 | 160° C. |
| Evaluation Example 2-6 | compound No. 172 | 160° C. |
| Evaluation Example 2-7 | compound No. 221 | 200° C. |
| Evaluation Example 2-8 | compound No. 247 | 230° C. |
| Comparative Example 1 | comparative compound 1 | 220° C. |
| Comparative Example 2 | comparative compound 2 | 210° C. |
| Comparative Example 3 | comparative compound 3 | 230° C. |
| Comparative Example 4 | comparative compound 4*[1] | 160° C. |
| Comparative Example 5 | comparative compound 5*[2] | 190° C. |
| Comparative Example 6 | comparative compound 6 | 290° C. |

*[1]The melting point was 160° C. or above, and thermal decomposition occurred without going through a liquid state.
*[2]The melting point was 185° C., and a stable liquid state could not be maintained.

A comparison of the results in Table 2 for alkoxide compounds Nos. 43, 49, 55, 75, 171, and 172 with those for comparative compounds 1 to 3 and a comparison of the results for alkoxide compounds Nos. 221 and 247 with those for comparative compound 6 demonstrated that alkoxide compounds Nos. 43, 49, 55, 75, 171, and 172 could undergo thermal decomposition at temperatures lower than for comparative compounds 1 to 3 and that alkoxide compounds Nos. 221 and 247 could undergo thermal decomposition at temperatures lower than for comparative compound 6. In addition, it was shown that alkoxide compounds Nos. 43, 49, 55, 75, 171, 172, and 221 had thermal decomposition temperatures of not more than 200° C., while alkoxide compounds Nos. 43, 49, 55, 75, 171, and 172 underwent thermal decomposition at temperatures below 200° C. It was also shown that comparative compound 4, while having a low initial thermal decomposition temperature, also had a melting point that was higher than its initial thermal decomposition temperature and thus could not support a liquid state. It was shown that comparative compound 5, while having a low initial thermal decomposition temperature just like comparative compound 4, had a melting point at a temperature very near its initial thermal decomposition temperature and was thus unable to maintain a stable liquid state. Alkoxide compound No. 171, which was evaluated in Evaluation Example 2-5, was a compound with a low initial thermal decomposition temperature and a melting point of 60° C., and alkoxide compound No. 172, which was evaluated in Evaluation Example 2-6, was a compound that had a low initial thermal decomposition temperature and that was in the liquid state at 30° C. Compounds that have a low melting point and a large temperature difference between their melting point and initial thermal decomposition temperature, can be easily maintained in the liquid state and require little energy for transport and are thus well suited as chemical vapor deposition starting materials.

Example 14: Production of Metallic Cobalt Thin Films by ALD Method

Figure 2:
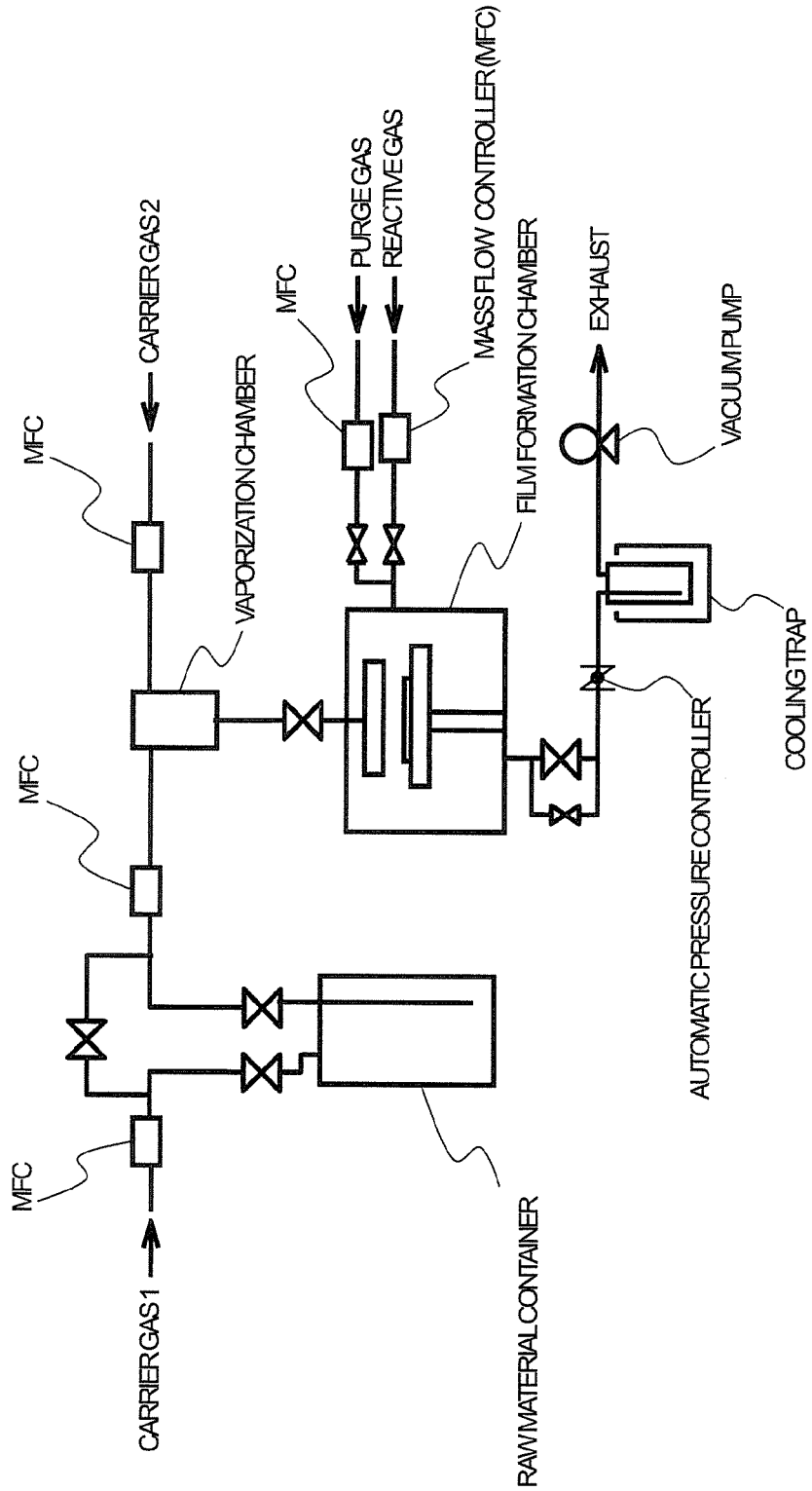
FIG. 2 is a schematic diagram that shows another example of the chemical vapor deposition apparatus used in the method according to present invention for forming a metal-containing thin film.

Metallic cobalt thin films were produced on silicon wafers using alkoxide compounds Nos. 43, 49, 55, and 75 as the chemical vapor deposition starting materials and using an ALD method under the conditions indicated below using the apparatus shown in FIG. 2. When the obtained thin films were submitted to measurement of the film thickness by X-ray reflectivity and identification of the thin film structure and thin film composition by X-ray diffraction and X-ray photoelectron spectroscopy, the film thickness was 2 to 4 nm, the film composition was metallic cobalt (identification by the Co 2p peak by XPS analysis), and the carbon content was less than the 0.1 atom % lower detection limit. The film thickness obtained per 1 cycle was 0.02 to 0.04 nm.

(Conditions)

reaction temperature (wafer temperature): 300° C.; reactive gas: hydrogen gas (Process)

The process chain composed of the following (1) to (4) was 1 cycle, and 100 cycles were performed.

(1) The chemical vapor deposition starting material is vaporized using conditions of a vaporizer temperature of 110° C. and a vaporizer pressure of 50 Pa, and the resulting vapor is introduced and deposition is carried out for 30 seconds at a system pressure of 50 Pa.

(2) The unreacted starting material is removed by an argon purge for 5 seconds.

(3) The reactive gas is introduced and a reaction is carried out for 30 seconds at a system pressure of 50 Pa.

(4) The unreacted starting material is removed by an argon purge for 5 seconds.

Example 15: Production of Metallic Copper Thin Films by ALD Method

Figure 3:
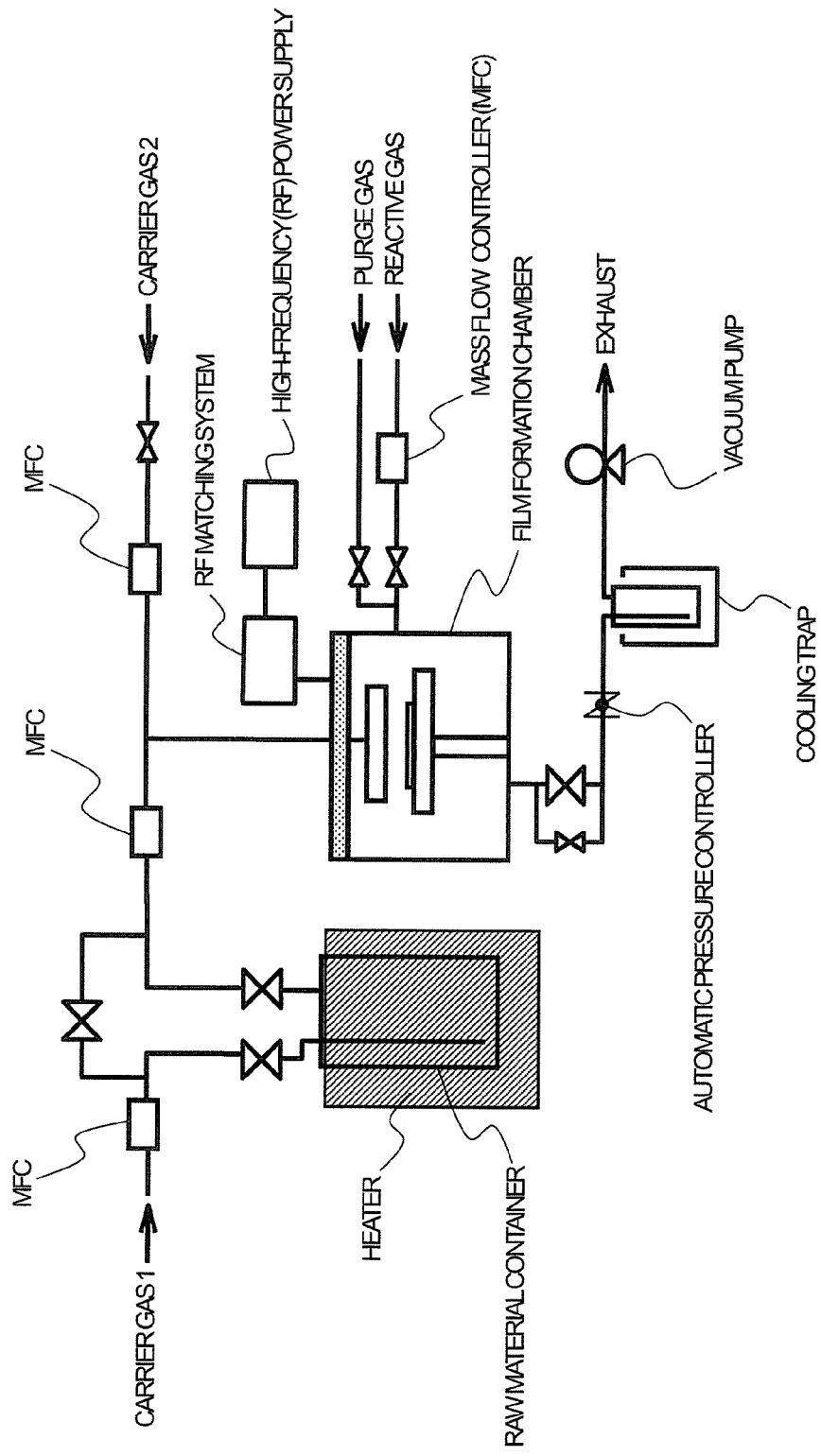
FIG. 3 is a schematic diagram that shows another example of the chemical vapor deposition apparatus used in the method according to the present invention for forming a metal-containing thin film.
Figure 4:
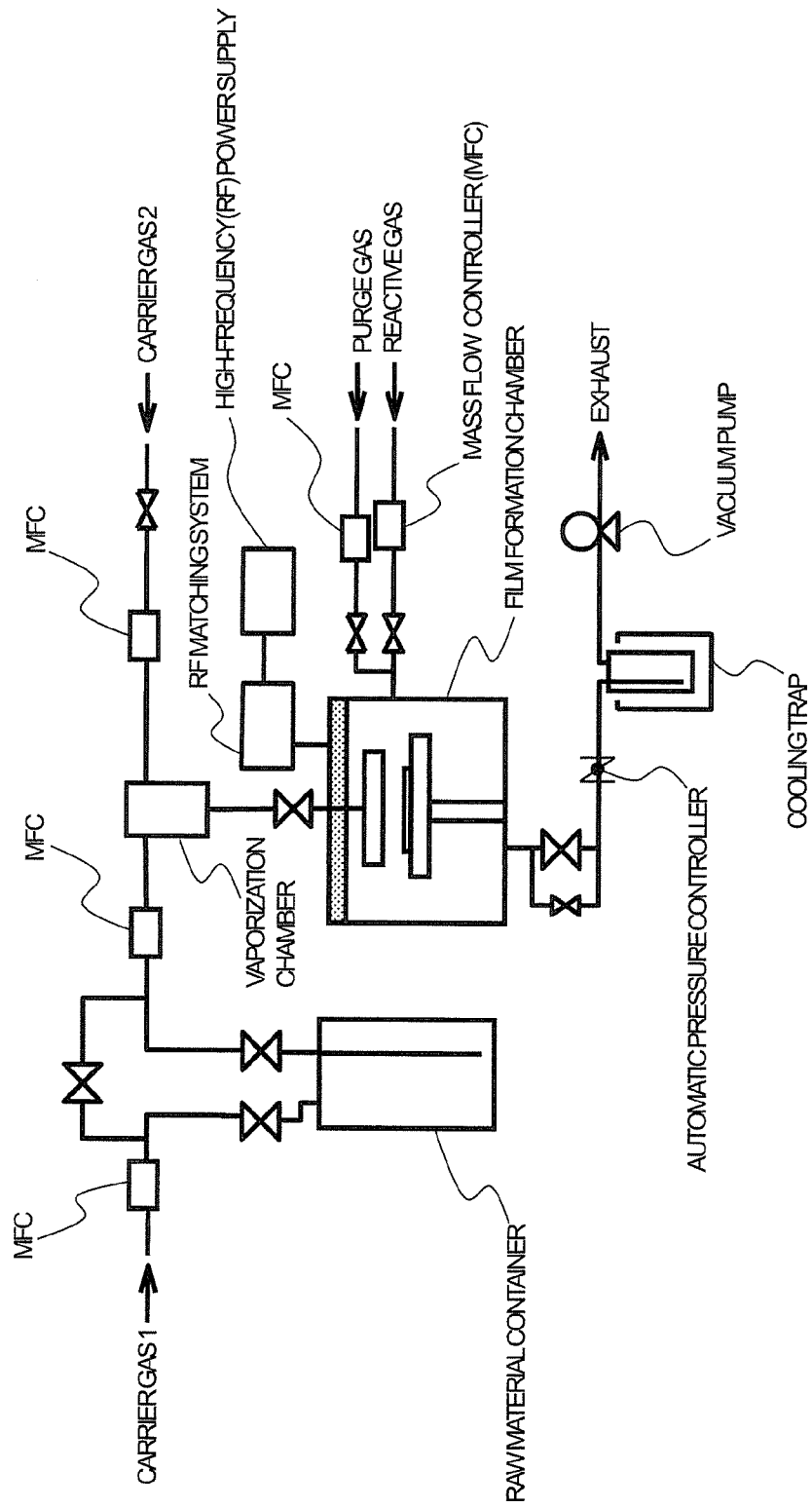
FIG. 4 is a schematic diagram that shows another example of the chemical vapor deposition apparatus used in the method according to the present invention for forming a metal-containing thin film.

Metallic copper thin films were produced on silicon wafers using alkoxide compounds Nos. 171 and 172 as the chemical vapor deposition starting materials and using a PEALD method under the conditions indicated below using a plasma deposition apparatus shown in FIG. 3. When the obtained thin films were submitted to measurement of the film thickness by X-ray reflectivity and identification of the thin film structure and thin film composition by X-ray diffraction and X-ray photoelectron spectroscopy, the film thickness was 2 to 4 nm, the film composition was metallic copper (identification by the Cu 2p peak by XPS analysis), and the carbon content was less than the 0.1 atom % lower detection limit. The film thickness obtained per 1 cycle was 0.02 to 0.04 nm.

(Conditions)

reaction temperature (wafer temperature): 60° C.; reactive gas: hydrogen gas; plasma output: 50 W (Process)

The process chain composed of the following (1) to (4) was 1 cycle, and 100 cycles were performed.

(1) The chemical vapor deposition starting material is vaporized using conditions of a heating temperature of 60° C. for the starting material container and a pressure within the starting material container of 50 Pa, and the resulting vapor is introduced and deposition is carried out for 30 seconds at a system pressure of 50 Pa.

(2) The unreacted starting material is removed by an argon purge for 5 seconds.

(3) The reactive gas and plasma are introduced and a reaction is carried out for 30 seconds at a system pressure of 50 Pa.

(4) The unreacted starting material is removed by an argon purge for 5 seconds.

Example 16: Production of Metallic Nickel Thin Films by ALD Method

Metallic nickel thin films were produced on silicon wafers using each of alkoxide compounds Nos. 221 and 247 as the chemical vapor deposition starting material and using a thermal ALD method under the conditions indicated below using the apparatus shown in FIG. 1. When the obtained thin films were submitted to measurement of the film thickness by X-ray reflectivity and identification of the thin film structure and thin film composition by X-ray diffraction and X-ray photoelectron spectroscopy, in each case the film thickness was 20 to 40 nm, the film composition was metallic nickel (identification by the Ni 2p peak by XPS analysis), and the carbon content and nitrogen content were less than the 0.1 atom % lower detection limit. The film thickness obtained per 1 cycle was 0.02 to 0.04 nm.

(Conditions)

reaction temperature (wafer temperature): 230° C.; reactive gas: hydrogen gas (Process)

The process chain composed of the following (1) to (4) was 1 cycle, and 1,000 cycles were performed.

(1) The chemical vapor deposition starting material is vaporized using conditions of a vaporizer temperature of 70° C. and a vaporizer pressure of 50 Pa, and the resulting vapor is introduced and deposition is carried out for 30 seconds at a system pressure of 50 Pa.

(2) The unreacted starting material is removed by an argon purge for 5 seconds.

(3) The reactive gas is introduced and a reaction is carried out for 30 seconds at a system pressure of 50 Pa.

(4) The unreacted starting material is removed by an argon purge for 5 seconds.

Example 17: Production of Metallic Nickel Thin Films by ALD Method

Metallic nickel thin films were produced on silicon wafers using each of alkoxide compounds Nos. 221 and 247 as the chemical vapor deposition starting material and using a PEALD method under the conditions indicated below using the plasma deposition apparatus shown in FIG. 3. When the obtained thin films were submitted to measurement of the film thickness by X-ray reflectivity and identification of the thin film structure and thin film composition by X-ray diffraction and X-ray photoelectron spectroscopy, in each case the film thickness was 50 to 70 nm, the film composition was metallic copper (identification by the Ni 2p peak by XPS analysis), and the carbon content and nitrogen content were less than the 0.1 atom % lower detection limit. The film thickness obtained per 1 cycle was 0.05 to 0.07 nm.

(Conditions)

reaction temperature (wafer temperature): 70° C.; reactive gas: hydrogen gas; plasma output: 50 W (Process)

The process chain composed of the following (1) to (4) was 1 cycle, and 1,000 cycles were performed.

(1) The chemical vapor deposition starting material is vaporized using conditions of a heating temperature of 70° C. for the starting material container and a pressure within the starting material container of 50 Pa, and the resulting vapor is introduced and deposition is carried out for 30 seconds at a system pressure of 50 Pa.

(2) The unreacted starting material is removed by an argon purge for 5 seconds.

(3) The reactive gas and plasma are introduced and a reaction is carried out for 30 seconds at a system pressure of 50 Pa.

(4) The unreacted starting material is removed by an argon purge for 5 seconds.

The invention claimed is:

1. An alkoxide compound of the following formula (I):

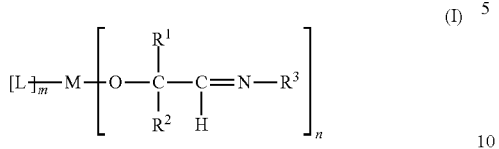

wherein $R^1$ and $R^2$ are each independently a hydrogen atom, a $C_{1-12}$ hydrocarbon group, or a group of any of the following formulas (X-1) to (X-8); $R^3$ is a hydrogen atom or a $C_{1-3}$ hydrocarbon group or a group of any of the following formulas (X-1) to (X-8); however, when $R^1$ is a methyl group and $R^2$ is a methyl group or an ethyl group, $R^3$ is a hydrogen atom or a group of any of the following formulas (X-1) to (X-8); L is a hydrogen atom, a halogen atom, a hydroxyl group, an amino group, an azido group, a phosphido group, a nitrile group, a carbonyl group, a $C_{1-12}$ hydrocarbon group, or a group of any of the following formulas (L-1) to (L-13); M is a metal atom that is copper, iron, nickel, cobalt or manganese; n is an integer equal to or greater than 1; m is an integer equal to or greater than 0; and n+m is the valence of the metal atom of M,

wherein $R^{X1}$ to $R^{X12}$ are each independently a hydrogen atom or a $C_{1-12}$ hydrocarbon group, and $A^1$ to $A^3$ are each a $C_{1-6}$ alkanediyl group,

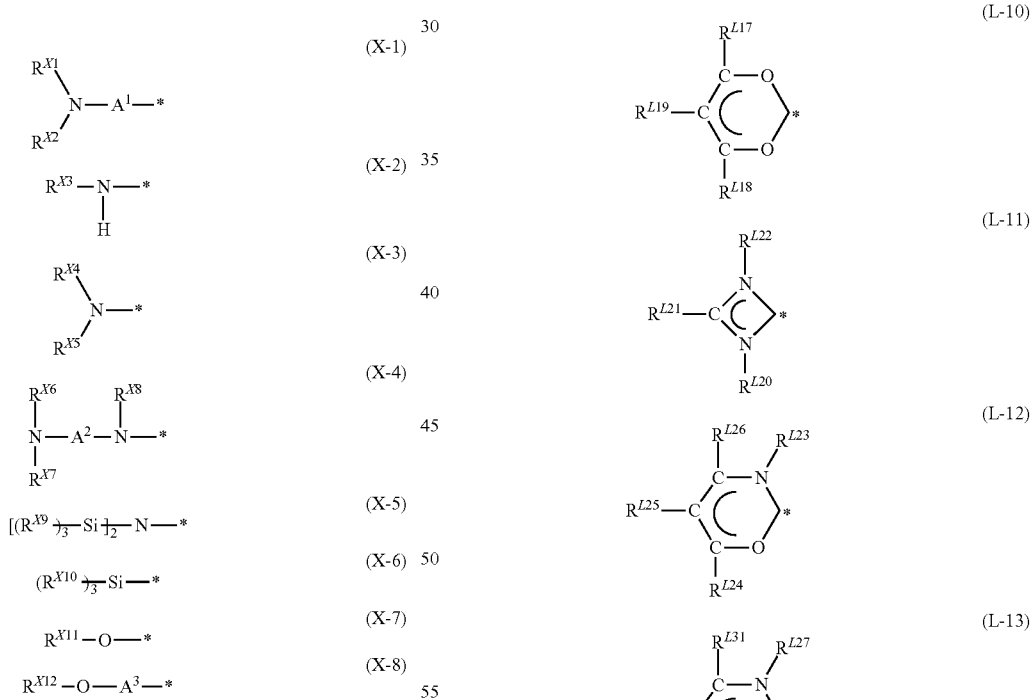

wherein $R^{L1}$ to $R^{L31}$ are each independently a hydrogen atom or a $C_{1-12}$ hydrocarbon group and $A^4$ to $A^7$ are each a $C_{1-6}$ alkanediyl group; when any of $R^{L1}$ to $R^{L31}$ is a $C_{1-12}$ hydrocarbon group, a hydrogen atom in the hydrocarbon group may be substituted by a halogen atom or an amino group.

2. A method of forming a thin film, comprising:
introducing, into a film-formation chamber in which a substrate is disposed, a vapor containing an alkoxide compound and obtained by vaporizing thin film-forming starting material comprising the alkoxide compound according to claim 1; and
forming a thin film containing at least one atom selected from the metal atom, on a surface of the substrate by decomposing and/or chemically reacting the alkoxide compound.

* * * * *